United States Patent
Pennypacker et al.

(10) Patent No.: US 9,636,311 B2
(45) Date of Patent: *May 2, 2017

(54) N,N'-DI-1 NAPHTHYLGUANIDINE HCL (NAGH) AND N,N'-DI-P-NITROPHENYLGUANIDINE HCL (NAD) TREATMENT FOR STROKE AT DELAYED TIMEPOINTS

(71) Applicants: Keith R. Pennypacker, Lexington, KY (US); Alison Willing, Tampa, FL (US); Javier Cuevas, Lutz, FL (US); Jon C. Antilla, Tampa, FL (US); Michelle Cortes-Salva, Fairfax, VA (US)

(72) Inventors: Keith R. Pennypacker, Lexington, KY (US); Alison Willing, Tampa, FL (US); Javier Cuevas, Lutz, FL (US); Jon C. Antilla, Tampa, FL (US); Michelle Cortes-Salva, Fairfax, VA (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,796

(22) Filed: Feb. 4, 2016

(65) Prior Publication Data

US 2016/0151311 A1    Jun. 2, 2016

Related U.S. Application Data

(60) Division of application No. 14/531,296, filed on Nov. 3, 2014, now abandoned, which is a continuation of application No. PCT/US2013/039301, filed on May 2, 2013.

(60) Provisional application No. 61/641,514, filed on May 2, 2012.

(51) Int. Cl.
*A61K 31/155* (2006.01)
*C07C 279/18* (2006.01)

(52) U.S. Cl.
CPC .......... *A61K 31/155* (2013.01); *C07C 279/18* (2013.01)

(58) Field of Classification Search
USPC ........................................................ 514/634
See application file for complete search history.

(56) References Cited

U.S. PATENT DOCUMENTS

| 6,673,557 B2* | 1/2004 | McBurney | A61K 31/155 424/427 |
| 2005/0020483 A1* | 1/2005 | Oksenberg | A61K 31/00 514/252.12 |
| 2007/0123556 A1* | 5/2007 | Pennypacker | A61K 31/00 514/289 |

FOREIGN PATENT DOCUMENTS

WO   WO2010048164   *  4/2010

OTHER PUBLICATIONS

Cortes-Salva et al. CAS: 2009: 1282271, 2009.*
Retinal Ischemia. Lasik Eye Surgery Correction. Date Accessed: Jan. 25, 2017. www.lasikeyesurgerycorrection.com/retinal-ischemia.html.
Moheet and Katzan. Disease Management: Stroke. Cleveland Clinic Center for Continuing Education. Date Published: Sep. 2013. www.clevelandclinicmeded.com/medicalpubs/diseasemanagement/neurology/ischemic-stroke/.

* cited by examiner

*Primary Examiner* — Rei-Tsang Shiao
(74) *Attorney, Agent, or Firm* — Michele L. Lawson; Smith & Hopen, P.A.

(57) ABSTRACT

A method of treating stroke by administration of a novel sigma agonist is presented. Twenty-four hours after MCAO, systemic administration of several novel sigma agonists including: Bromo-DTG; Chloro-DTG; N,N'-di-1-Naphthylguanidine hydrochloride (NAGH); N,N'-di-p-Nitrophenylguanidine HCL (NAD) or vehicle were injected subcutaneously daily for 3 days. Rats treated with Bromo-DTG and Chloro-DTG had no significant improvements in any of the motor or cognitive tests while NAGH treated rats showed improved vertical movement and had significantly less motor asymmetry and bias than vehicle treated rats. Sigma receptor agonist NAGH also was found to exert its long-term neuroprotective effects by preserving both gray matter and white matter tracts. Both NAD and NAGH, when administered 24 hours after experimental stroke, reduced neural damage and enhanced behavioral recovery thirty days later which suggests that NAGH and NAD potentially extend the therapeutic window of stroke several fold over the current treatments.

20 Claims, 22 Drawing Sheets

N,N'-DI-1 NAPHTHYLGUANIDINE HCL (NAGH) AND N,N'-DI-P-NITROPHENYLGUANIDINE HCL (NAD) TREATMENT FOR STROKE AT DELAYED TIMEPOINTS

CROSS REFERENCE TO RELATED APPLICATIONS

This application is a divisional of and claims priority to currently pending U.S. patent application Ser. No. 14/531,296, entitled "N,N'-Di-1 Naphthylguanidine HCl (NAGH) and N,N'-Di-P-Nitrophenylguanidine HCl (NAD) Treatment For Stroke at Delayed Timepoints", filed Nov. 3, 2014, which is a continuation of and claims priority to International Patent Application No. PCT/US2013/039301, filed on May 2, 2013 which claims priority to U.S. Provisional Patent Application No. 61/641,514, entitled "N,N'-Di-P-Nitrophenylguanidine HCL Reduces Infarct Volume and Increases Functional Recovery After Stroke", filed on May 2, 2012, the contents of each of which are herein incorporated by reference.

FIELD OF INVENTION

This invention relates to stroke treatment. Specifically, the invention discloses a novel treatment of stroke using sigma receptors.

BACKGROUND OF THE INVENTION

Stroke poses a significant healthcare burden in this country as it is the fourth leading cause of death and results in a significant amount of chronic disability (Towfighi and Saver 2011). Despite decades of research, there is presently no approved drug-based therapy that stimulates recovery of neurological functions in stroke patients (Endres, Engelhardt et al. 2008).

Several pharmacological drugs, such as carbamylate erythropoietin (Villa, van Beek et al. 2007), granulocyte-colony stimulating factor (Schabitz and Schneider 2006) and amphetamine (Barbay and Nudo 2009) enhance functional recovery and are currently being evaluated in clinical trials for stroke recovery. However, results from pharmacological studies suggest that multiple mechanisms contribute to different aspects of functional recovery and therefore several mechanisms must be targeted in developing stroke drug therapies to provide optimal functional restoration. Recently one research group found a selective sigma receptor agonist, SA4503, enhanced brain plasticity and improved sensorimotor function without decreasing infarct size (Ruscher, Shamloo et al. 2011). The researchers concluded that SA4503 may exert neuroprotective effects by enhancing cellular trafficking of biomolecules essential for brain repair.

Sigma receptors ($\sigma$Rs) are predominantly expressed at the endoplasmic reticulum (ER) and represent a structurally unique class of intracellular proteins that function as chaperones (Katz, Su et al. 2011). Ajmo and collaborators (Ajmo, Vernon et al. 2006) showed that the $\sigma$-1/$\sigma$-2 ligand N,N'-di-o-tolyl guanidine (DTG) decreases infarct size in a rat model of ischemic stroke. The authors suggested that this neuroprotective effect of DTG was probably due in part to the preservation of intracellular calcium homeostasis. The authors also showed that DTG dampened pro-inflammatory signals at delayed time points by decreasing the number of activated microglia and astrocytes, thereby preventing expansion of the ischemic core. When administered beginning 24 hours after permanent middle cerebral artery occlusion (MCAO), 1,3-di-o-tolylguanidine (DTG) decreased infarct size 96 hrs post-MCAO, but failed to improve long-term functional recovery (Leonardo, Hall et al. 2010).

Most rodent stroke studies have focused on mechanisms of neuronal injury and neuroprotection, and have largely neglected white matter injury following stroke. The inventors believe that drugs targeted only to gray matter will not be efficient in minimizing damage or sustaining functional recovery following stroke. White matter comprises 50% of human brain, is more sensitive to oxidative stress than neurons and is as equally affected as neurons in most cases of stroke (Ho, Reutens et al. 2005). It does not matter how many neurons are spared by a treatment, if there remains extensive damage to oligodendrocytes and white matter tracts, functional recovery will not be possible.

Sigma receptor ($\sigma$1R) agonist 1,3 di-o-tolylguanidine [DTG] decreased infarct volume in rats 96 hours after stroke, but the effect was not maintained long-term, and therefore, did not improve behavioral outcomes (Leonardo, Hall et al. 2010). Of the thousands of promising treatments tested in animals, the clot busters, tissue plasminogen activator (tPA) which restore blood flow remain as the only FDA approved drug. However, most patients do not receive tPA as they seek treatment beyond the narrow therapeutic window. Moreover, these drugs do not treat any of the pathophysiologic processes occurring after stroke. So it is an unmet need to target pathological process occurring at delayed time points after stroke.

What is needed is a composition and method of treating neurological disorders such as stroke which improves optimal long-term functional recovery.

SUMMARY OF INVENTION

The inventors have developed a novel method for treating stroke at a delayed timepoint comprising administering a therapeutically effective amount of a novel sigma agonist selected from the group consisting of N,N'-di-1-Naphthylguanidine hydrochloride (NAGH) or N,N'-di-p-Nitrophenylguanidine hydrochloride (NAD) to a patient in need thereof. The sigma agonist can be administered at least 12 hours after stroke. The sigma agonist may be NAGH and be administered in a therapeutically effective amount of between about 0.86 mg/kg and 8.6 mg/kg at least once per day for at least 3 days.

In an alternative embodiment, the sigma agonist may be NAD and be administered in a therapeutically effective amount of between about 2.8 mg/kg and 8.6 mg/kg at least once per day for at least 3 days.

In another embodiment, a method of reducing infarct volume long term in a patient suffering from a neurological disorder is presented comprising administering a therapeutically effective amount of a novel sigma agonist selected from the group consisting of N,N'-di-1-Naphthylguanidine hydrochloride (NAGH) or N,N'-di-p-Nitrophenylguanidine hydrochloride (NAD) to a patient in need thereof. The neurological disorder may be stroke and the sigma agonist may be administered at least 12 hours after stroke. In an embodiment, the sigma agonist is NAGH administered in a therapeutically effective amount of between about 0.86 mg/kg and 8.6 mg/kg at least once per day for at least 3 days.

In an alternative embodiment, the sigma agonist may be NAD and be administered in a therapeutically effective amount of between about 2.8 mg/kg and 8.6 mg/kg at least once per day for at least 3 days.

In an embodiment, the inventors administered a newly synthesized mixed sigma 1/2 receptor agonist, N,N'-di-1-Naphthylguanidine hydrochloride (NAGH) beginning about 24 hour post-stroke and performed a battery of behavioral tests to evaluate its effects on long-term behavioral outcomes and the pathological processes occurring at delayed time points after stroke onset. The data show that NAGH improved motor function, decreased the number of activated microglia, and protect demyelination following stroke in particular in the cortical area without decreasing the infarct volume. Taken together, the results showed that NAGH improved behavioral recovery 30 days after MCAO via preservation of both gray matter and white matter tracts.

Although many preclinical studies have focused on a small time window after the experimental stroke to evaluate functional outcome, the inventors evaluated long-term behavioral outcomes at 30 days after MCAO to assess functional recovery. Male Sprague-Dawley rats were subcutaneously injected daily with either a mixed sigma 1/2 receptor agonist; N,N'-di-1-Naphthylguanidine hydrochloride (NAGH) (n=42/group) or with vehicle (40% DMSO) for three days starting at 24 hours post-stroke.

The inventors examined the long-term therapeutic effects of NAGH on infarct volume and white matter tracts as well as motor recovery. Infarct volume in the stroke group receiving vehicle only (n=25) was 17.57±4.43%, whereas animals receiving NAGH (n=27) showed infarcts involving 13.58±2.3% of the hemisphere (p>0.05). The NAGH treated rats show improved vertical movement and had significantly less motor asymmetry and bias than vehicle treated rats (*p<0.05). Further, the results demonstrated a larger loss of Luxol-fast blue staining (*p<0.05) within the subcortical and striatal white matter in animals treated with DMSO compared to NAGH treated animals.

The inventors discovered that sigma receptor agonist NAGH exerts its long-term neuroprotective effects by preserving both gray matter and white matter tracts. Pharmacological targeting of the sigma receptor provides new opportunities to open new avenues in developing stroke treatment.

Another newly synthesized mix of σ1/σ2Rs agonist, N,N'-di-p-nitrophenylguanidine HCL (NAD) was developed based on the structure of DTG that also induced sustained functional recovery, enhanced behavioral recovery, and decreased infarct size when compared to DTG.

The systemic administration of N,N'-di-p-nitrophenylguanidine HCL (NAD) when administered 24 hours after experimental stroke was found to reduce neural damage and more importantly, enhance behavioral recovery thirty days later. This agent has the potential to extend the therapeutic window several-fold over the current one to open treatment to many stroke patients. Additionally, this agent provides neural protection leading to recovery of functions, such as motor skills. The approved treatment, tissue plasminogen activator acts only as a clot buster and does not possess any neural protective properties.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
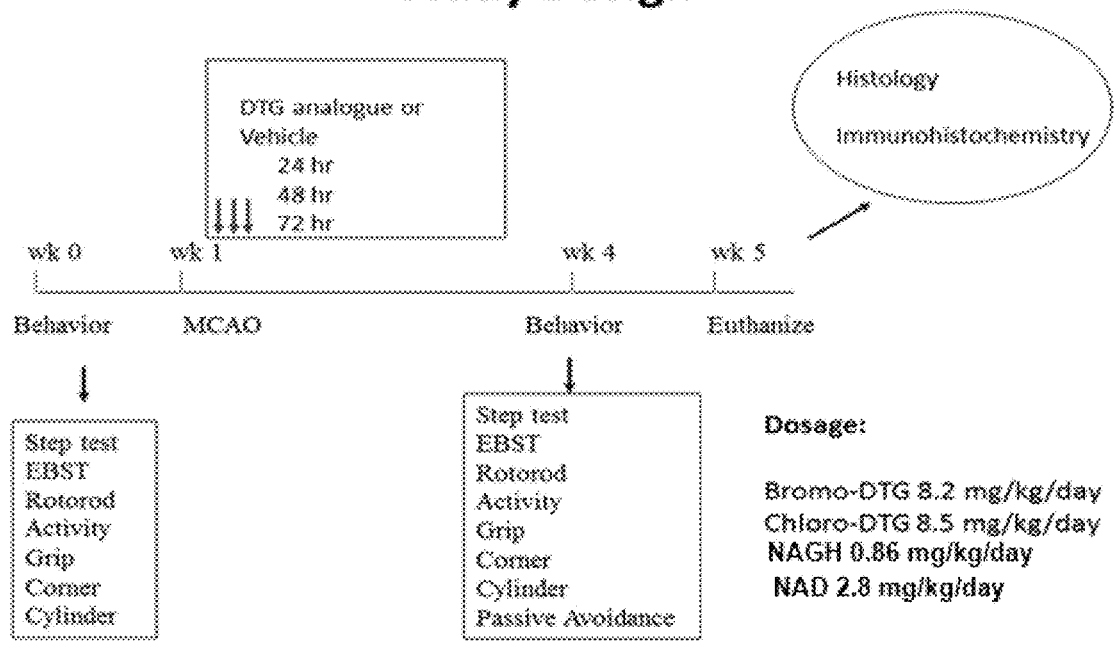
FIG. 1 is a diagram of the experimental design used to test the compounds used in the present invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

DEFINITIONS

NAGH is used interchangeably herein with NAPH, NAPH-DTG and N—N-NAPH and is an acronym for N,N'-di-1-Naphthylguanidine hydrochloride.

NAD is used interchangeably herein with NDH, NDH-DTG and Nitro-DTG and is an acronym for N,N'-di-p-Nitrophenylguanidine hydrochloride.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

"Composition" is used herein interchangeably with "compound", "drug", "formulation" and "molecule".

"Patient" is used to describe an animal, preferably a human, to whom treatment is administered, including prophylactic treatment with the compositions of the present invention. "Patient" includes both mammals and non-mammals including, but not limited to, humans; non-human primates; bovines; domestic animals such as rabbits, dogs, and cats; laboratory animals such as rats, mice and guinea pigs; and non-mammals such as birds and fish.

The "therapeutically effective amount" for purposes herein is thus determined by such considerations as are known in the art. A therapeutically effective amount of a composition, or mixture of compositions thereof, is that amount necessary to provide a therapeutically effective result in vivo. The amount of sigma agonist or any combination of sigma agonists thereof must be effective to achieve a response, including but not limited to total prevention of (e.g., protection against) and to improved survival rate or more rapid recovery, or improvement or elimination of symptoms associated with neurological disorders or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. An "effective amount" for therapeutic purposes is the amount of the composition of sigma receptor ligand required to provide a clinically significant decrease in neurodegenerative disease, such as those resulting from ischemic stroke. One of skill in the art can readily determine appropriate single dose sizes for systemic administration based on the size of a mammal and the route of administration.

"Administration" or "administering" is used to describe the process in which the compositions or any combination of compositions thereof of the present invention are delivered to a patient. Compositions of this invention can be administered as pharmaceutical compositions, including those suitable for oral, including buccal and sub-lingual; rectal; nasal; topical; pulmonary; vaginal; or parenteral, including intramuscular, intra-arterial, intrathecal, subcutaneous, and intravenous.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19th ed.) describes formulations which can be used in connection with the subject invention.

For ease of administration, the subject compounds may be formulated into various pharmaceutical forms. As appropriate compositions there may be cited all compositions usually employed for systemically administering drugs. To prepare the pharmaceutical compositions of this invention, the sigma agonist, as the active ingredient is combined with a pharmaceutically acceptable carrier, which may take a wide variety of forms depending on the form of preparation desired for administration. Compounds of this invention can be administered as pharmaceutical compositions, including those suitable for oral, including buccal and sub-lingual; rectal; nasal; topical; pulmonary; vaginal; or parenteral, including intramuscular, intra-arterial, intrathecal, subcutaneous, and intravenous. In some embodiments, intravenous or intra-arterial administration is a preferred manner of providing a daily dosing regimen that can be adjusted according to the degree of affliction. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition such as stroke. For example, the dosage of a compound of the invention administered can be between about 0.01 mg/kg to about 10.0 mg/kg. Typically, the dosage of NAGH can be in the range of about 0.86 mg/kg to about 8.6 mg/kg when given on a daily schedule. It is contemplated that one of ordinary skill in the art can determine and administer the appropriate dosage of compounds disclosed in the current invention according to the foregoing considerations.

Dosing frequency for the composition includes, but is not limited to, at least about 1 day, at least about 2 days, at least about 3 days, at least about 4 days, at least about 5 days, at least about 6 days and at least about 7 days. In some embodiments, the interval between each administration is constant. For example, the administration can be carried out daily, every two days, every three days, every four days, every five days, or weekly. For example, in an embodiment using NAGH, the dosing frequency for the composition is once per day for between about 3 to about 7 days after stroke starting at least about 12 hours post-stroke. In some embodiments, the administration can be carried out twice daily, three times daily, or more frequent. Administration can also be continuous and adjusted to maintaining a level of the compound within any desired and specified range.

When used to treat symptoms of a neurological disease such as ischemia or stroke, the compounds may be administered at any time after occurrence of the neurological disease. A defined time period may pass before administration of the compound. In the case of stroke, this defined time period may be at least 3 hours post-stroke, at least 6 hours post-stroke, at least 9 hours post-stroke, at least 12 hours post-stroke, at least 24 hours post-stroke, at least 48 hours post-stroke, at least 72 hours post-stroke, at least 96 hours post-stroke, at least 7 days post-stroke, at least 14 days post-stroke, at least 21 days post-stroke, and at least 30 days post-stroke. Administration of the compound includes all time periods between those listed above to the hour.

The compounds used in the present invention may be administered individually, or in combination with or concurrently with one or more other compounds used in other embodiments of the present invention. Additionally, compounds used in the present invention may be administered in combination with or concurrently with other therapeutics for neurological disorders such as stroke.

The term "agonist" as used herein is defined as a molecule, such as a compound, drug, enzyme activator, or hormone, which enhances the activity of another molecule or the activity of the sigma receptor site.

The term "antagonist" as used herein is defined as a molecule, such as a compound, drug, enzyme activator, or hormone, which diminishes or prevents the action of another molecule or the activity of the sigma receptor site.

"Neurological disorder" and "neurological disease" are used interchangeably throughout. Neurological disorder/neurological disease as used herein refers to a disorder which is caused by damage to the central nervous system and results in any abnormal physical or mental behavior or experience where the death or dysfunction of neuronal cells is involved in the etiology of the disorder. Both stroke and ischemia are considered neurological disorders as used herein.

The term "stroke" as used herein is defined broadly as the development of neurological deficits associated with impaired blood flow to the brain regardless of cause. Potential causes include, but are not limited to, thrombosis, hemorrhage and embolism. Other injuries that can result in stroke include aneurysm, angioma, blood dyscrasias, cardiac failure, cardiac arrest, septic shock, head trauma, spinal cord trauma, seizure, bleeding from a tumor or other blood loss.

The term "ischemic" or "ischemic episode" means any circumstance that results in a deficit of blood supply to a tissue, especially the central nervous system (CNS) or brain tissue. When the ischemia is associated with a stroke, it can be either global or focal ischemia. The term "ischemic stroke" means a type of stroke that is of limited extent and caused by a blockage of blood flow. Non-limiting examples include cerebral ischemia, ischemia after cardiac arrest, stroke, multi-faceted dementia, and complications from surgery. Cerebral ischemic episodes result from a deficiency in blood supple to the brain. The spinal cord is also considered part of the CNS, and is equally susceptible to ischemia resulting from diminished blood flow. The term "focal ischemia" is used to refer to a condition resulting from a blockage of a single artery that supplies blood to the brain or spinal cord, resulting in damage to the cells in the territory supplied by that artery. Conversely, "global ischemia" refers to a condition that results from a general diminution of blood flow to the entire tissue, such as the entire brain, forebrain, or spinal cord, thereby causing the death of neurons in selectively vulnerable regions throughout these tissues.

"Treatment" or "treating" as used herein refers to any of: the alleviation, amelioration, elimination and/or stabilization of a symptom, as well as delay in progression of a symptom of a particular disorder, namely a neurodegenerative disease or disorder such as stroke. For example, "treatment" of stroke may include any one or more of the following: amelioration and/or elimination of one or more symptoms associated with stroke, reduction of one or more symptoms of stroke, stabilization of symptoms of stroke, and delay in progression of one or more symptoms of stroke.

The term "long term" as used herein refers to a time period that is greater than 25 hours. In some embodiments, the term applies to a time period of at least 3 days, at least 5 days, at least 7 days, at least 10 days, at least 14 days, at least 18 days, at least 21 days, at least 25 days, at least 30 days, at least 2 months, at least 3 months, at least 4 months, at least 5 months, at least 6 months, at least 7 months, at least 8 months, at least 9 months, at least 10 months, at least 11 months, at least 12 months, and greater than one year. The time periods listed are exemplary and include all intervening days not specifically listed in 1 day increments.

The term "delayed timepoint" as used herein refers to a timepoint that is at least 3 hours after occurrence of a neurological disorder such as stroke. In the case of stroke, the delayed timepoint may be at least 3 hours post-stroke, at least 6 hours post-stroke, at least 9 hours post-stroke, at least 12 hours post-stroke, at least 24 hours post-stroke, at least 48 hours post-stroke, at least 72 hours post-stroke, at least 96 hours post-stroke, at least 7 days post-stroke, at least 14 days post-stroke, at least 21 days post-stroke, and at least 30 days post-stroke. Administration of the compound includes all time periods between those listed above to the hour. In some embodiments, the delayed timepoint is 24 hours post-stroke.

The inventors have previously shown that human umbilical cord blood cells provided long-term neuroprotection and improved functional recovery at 30 days in animals following stroke via its neuroprotective and anti-inflammatory properties (Chen, Sanberg et al. 2001; Vendrame, Cassady et al. 2004; Vendrame, Gemma et al. 2005). Sigma receptor agonists may mimic these effects and play a potential role in expanding the therapeutic window for stroke treatment. It was shown previously that sigma receptor agonists reduced neurodegeneration and enhanced neurosurvival following ischemic insult by decreasing ischemia-induced intracellular calcium elevations (Zhang and Cuevas 2002; Zhang and Cuevas 2005; Katnik, Guerrero et al. 2006), depressing inflammatory responses (Leonardo, Hall et al. 2010), and modulating immune responses specially by regulating microglial activation (Hall, Herrera et al. 2009). A recent study found that sigma receptor genes are upregulated in rat brains following injury when the rats were housed in an enriched environment (Ruscher, Shamloo et al. 2011). Moreover, this enriched environment increases neurogenesis in the hippocampus during stroke recovery (Ohlsson and Johansson 1995; Nygren, Wieloch et al. 2006). It was reported further that this enriched environment upregulates the genes associated with lipid synthesis and transport (Ruscher, Shamloo et al. 2011). It is well known that the sigma receptor is a membrane spanning cholesterol binding protein detected in the lipid rafts which act as a vehicle for cellular trafficking (Palmer, Mahen et al. 2007). They have also been found responsible for delivering myelin into the plasma (Jahn, Tenzer et al. 2009). Sigma receptors may play a greater role in regulating myelin trafficking following ischemic injury.

It was shown previously that MCAO produces locomotor and stereotypic hyperactivity with decreased resting time leading the animals to be more active than before the stroke (Janac, Radenovic et al. 2006). A battery of behavioral tests was performed to determine whether the efficacy of NAGH in reducing stroke-induced neural injury leads to functional recovery. There were significant improvements in function on a number of behavioral measures in rats treated with NAGH. The most significant finding was that NAGH treatment resulted in improvements in motor asymmetry in the EBST while non-treated animals exhibited functional impairment at 30 days post MCAO; this test has been used many times to evaluate sensorimotor asymmetry after focal brain ischemia (Borlongan, Hida et al. 1998). Treated animals were significantly less active than non-treated animals during both the dark and the light phases of the light cycle.

Previous studies provided much evidence that vertical movement and body asymmetry are strongly correlate to the size of infarct volume and neuronal recovery following stroke (Shen and Wang 2010; Encarnacion, Horie et al. 2011). Significant improvement was shown in all parameters of vertical movement except daytime VMN, and a significant improvement in body asymmetry in animals treated with NAGH.

It has been found that microglial cells are highly susceptible to ischemic injury (Jin, Yang et al. 2010). It has been further reported that microglia transform from a resting state to an activated state in response to neuronal injury (Kettenmann, Hanisch et al. 2011). The exact role of microglial cells after injury and repair is still unclear despite important progress in the understanding of microglial activation, proliferation, phagocytosis function, cytokines and growth factors production. It was found that stimulation of sigma receptors can reduce the production of cytokines and microglial activation in response to various stimuli including adenosine triphosphate (ATP), monocyte chemoattractant protein 1 (MCP-1), and lipopolysaccharide (LPS) (Hall, Leonardo et al. 2009). DTG inhibited ATP and UTP-evoked microglial migration when cells are pre-incubated in media containing metaphit, a pan-selective irreversible sigma receptor antagonist (Cuevas, Rodriguez et al. 2011). When the effects of DTG on microglial cell survival in response to in vitro ischemia was examined, it was found that DTG significantly reduced microglial cell death 24 hours after ischemia suggesting that DTG can be glial protective at delayed time points.

Almost all cases of ischemic stroke in humans involve white matter (Dewar, Underhill et al. 2003). Recent evidence suggests development of new drugs that only target excitotoxicity (Ikonomidou and Turski 2002), oxidative stress (Wang and Shuaib 2007), or inflammation (Kennedy and Vinten-Johansen 2006) are likely to fail, at least in part due to the lack of emphasis on white matter injury. Moreover, lower blood flow and less collateral blood supply in the deep white matter tracts make it more vulnerable to ischemia than gray matter (Lo, Dalkara et al. 2003). It was previously shown that human umbilical cord blood cells promote the expression of myelin-associated and antioxidant genes in cultured primary oligodendrocytes exposed to hypoxia-ischemia (Rowe, Leonardo et al. 2010). Therefore, a gene chip microarray analysis is needed to examine changes in gene expression in oligodendrocytes induced by NAGH. Previous results found that brain ischemia enhances proliferation of immature oligodendrocytes in the regions surrounding the lateral ventricle but decreases the number of mature oligodendrocytes in the per-infarct area (Mandai, Matsumoto et al. 1997).

The inventors sought to develop new sigma agonists, using DTG as the base molecule for manipulation, that induce more sustained functional recovery than DTG. The inventors investigated the following novel sigma ligands: N,N'-di-p-Bromophenylguanidine hydrochloride (Bromo-DTG; 8.2 mg/kg/day), N,N'-di-m-Chlorophenylguanidine hydrochloride (Chloro-DTG; 8.5 mg/kg/day), N,N'-di-1-Napthylguanidine hydrochloride (NAGH 0.86 mg/kg/day) and N,N'-di-p-Nitrophenylguanidine hydrochloride (NAD 2.8 mg/kg/day).

While all of the above drugs decreased infarct volume, the NAGH-DTG agonist is the only sigma receptor agonist in this series that induces long term motor recovery. The inventors found animals receiving NAGH spent significantly less time moving vertically during their day time activity. Nighttime vertical movement was also significantly enhanced in stroke animals receiving NAGH ($p<0.05$ vs. vehicle group). Moreover, Luxol Fast blue demonstrated that white matter tracts were more intact in the NAGH treated group, particularly in cortex. The data here showed that NAGH tended to decrease the number of Iba1-expressing cells in the ipsilateral hemisphere of the treated rats compared to the vehicle treated rats. The effect may be more robust with a different dosing regimen of the NAGH. Taken together, the data suggest that NAGH protected both neurons and oligodendrocytes from MCAO-induced cell death and is a good molecule for development as a stroke therapy.

Animals:

All animal procedures were performed according to the University of South Florida guidelines for the care and use of animals and protocols were reviewed and approved by the Institutional Animal Care and Use Committee and adhered to the NIH guidelines for the care and use of animals. Adult male Sprague Dawley rats (Harlan) weighing about 250-300 g at the time of surgery were used for the study. All animals were housed two per cage in a temperature controlled room, under a 12 hour light-dark cycle, and given access to water and food ad libitum. Animals were monitored daily for wellness and biweekly for weight loss. For the NAGH studies, a total of 84 animals were randomly assigned to 2 groups: MCAO only (n=42) and rat treated with NAGH (n=42) beginning 24 hour after MCAO.

Prior to MCAO induction and then again at 1 month post HUCB transplantation, animals were tested with a battery of standard functional tests as previously described (Vendrame M, Cassady C J, Newcomb J, Butler T, Pennypacker K R, Zigova T, et al. Stroke. 2004; 35:2390-5; Willing A E, Lixian J, Milliken M, Poulos S, Zigova T, Song S, et al. J Neurosci Res. 2003; 73(3):296-307), and as seen below. This was used as a baseline for treatment.

MCAO

MCAO surgeries were performed as described elsewhere (Vendrame M, Cassady C J, Newcomb J, Butler T, Pennypacker K R, Zigova T, et al. Stroke. 2004; 35:2390-2395). Briefly, rats were anesthetized with isoflurane, and the right common carotid and external carotid arteries were exposed using blunt dissection techniques. The vagus nerve was separated from common carotid artery and the external carotid artery was ligated proximally, and transected near the bifurcation. An embolus 40 mm in length (4.0 siliconized monofilament) was inserted into the external carotid artery and fed distally into the origin of the middle cerebral artery (~25 mm from insertion) through the internal carotid artery. Blood samples were taken and analyzed using an i-STAT handheld analyzer for hemoglobin, hematocrit, ionized calcium, glucose, sodium, potassium, pH, $pCO_2$, $HCO_3$, $TCO_2$, base excess, $pO_2$, and $O_2$. Cerebral blood flow was recorded using a Laser Doppler Monitor (Moor Instruments) to verify occlusion. Afterwards, the embolus was ligated permanently into the vessel and the neck incision was closed. Animals were treated with Ketoprofen IM (10 mg/kg) for three days post-surgery.

Drug Dosing Schedule

For the NAGH studies, vehicle or NAGH were prepared fresh each day. Daily subcutaneous injections (s.c) were administered beginning about 24 hours after MCAO and continued daily to about 72 hours post-surgery (FIG. 1). Animals received a total of 3 injections. A total of 84 animals were randomly assigned into 2 groups: Rats treated with vehicle (40% DMSO in sterile saline, n=42), or rats treated with 0.86 mg/kg NAGH (n=42).

Figure 9:
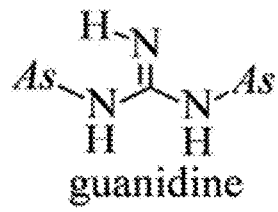
FIG. 9 is a diagram of the different compounds tested. DTG is 1,3-di-o-tolylguanidine; Bromo-DTG is N,N'-di-p-Bromophenylguanidine hydrochloride, Chloro-DTG is N,N'-di-m-Chlorophenylguanidine hydrochloride, NAGH is N,N'-di-1-Naphthylguanidine hydrochloride; and NAD is N,N'-di-p-Nitrophenylguanidine hydrochloride.
Figure 9:
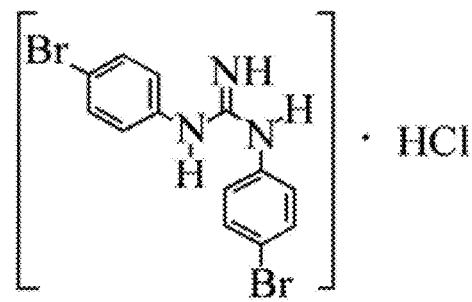
Figure 9:
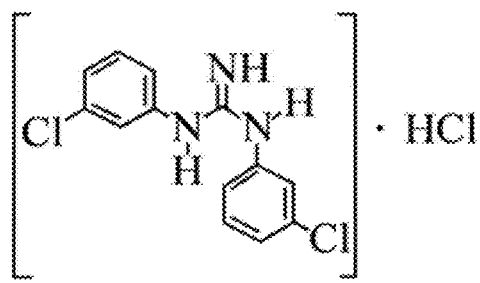
Figure 9:
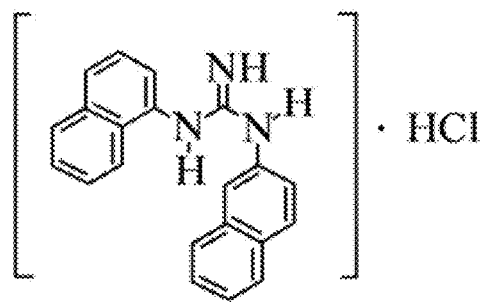
Figure 9:
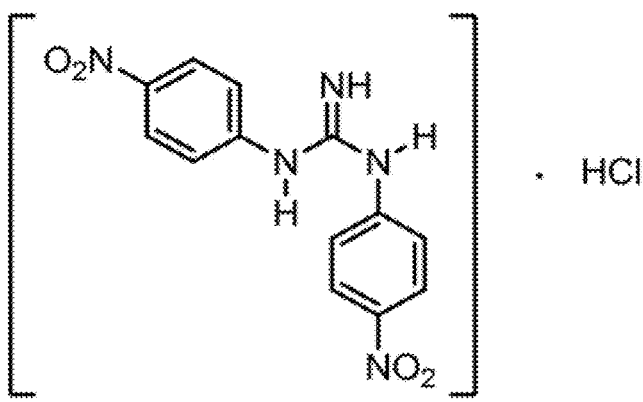
Figure 10:
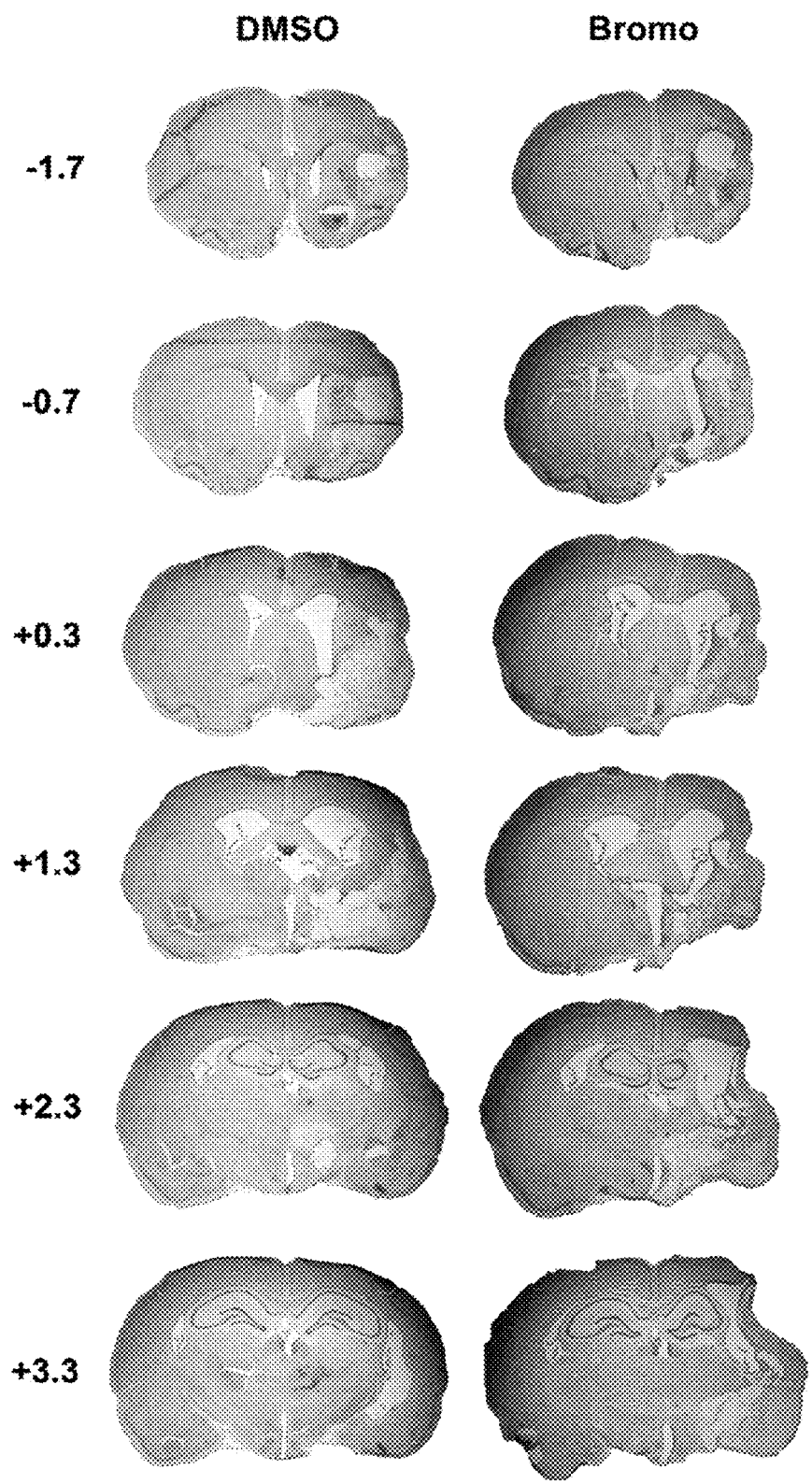
FIG. 10 is an image showing the effect of treatment with Bromo-DTG on Thionin staining throughout the brain hemispheres compared to animals without Bromo-DTG treatment.
Figure 11:
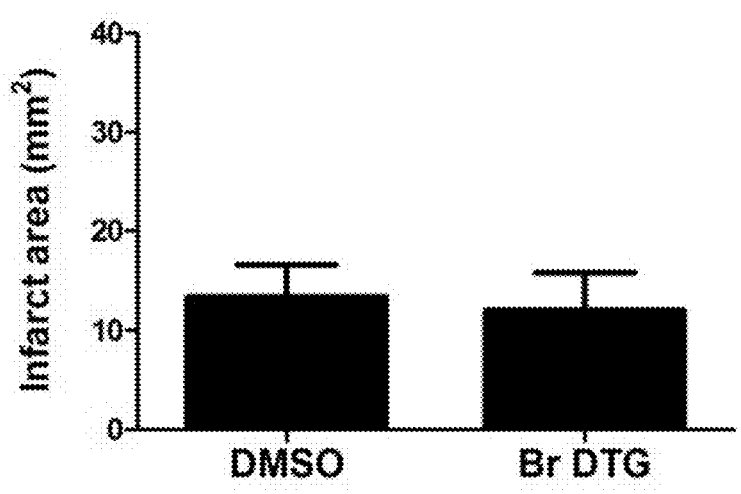
FIG. 11 is a graph showing the infarct volume in the stroke group receiving vehicle only versus Bromo-DTG treatment.
Figure 12:
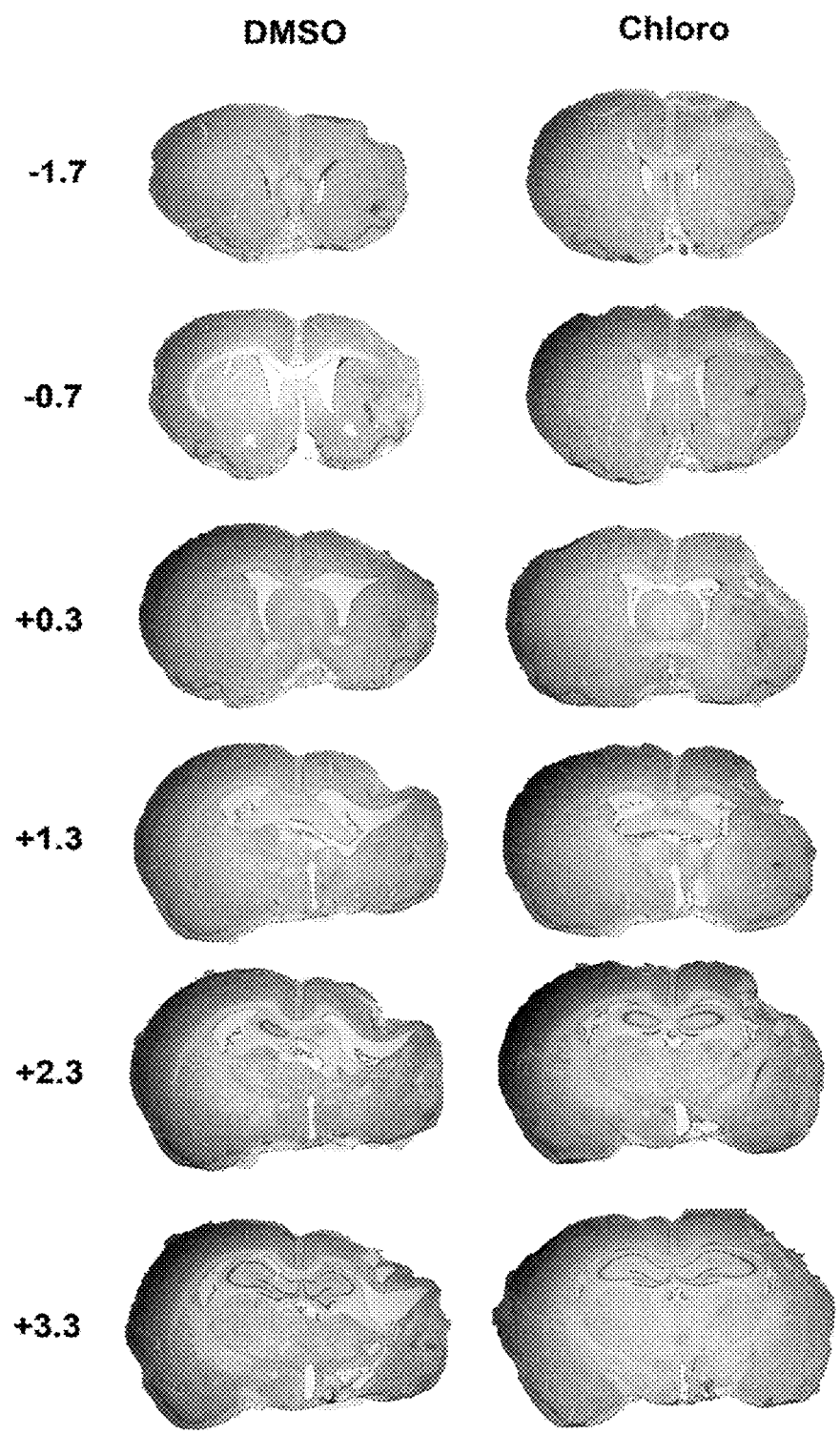
FIG. 12 is an image showing the effect of treatment with Chloro-DTG on Thionin staining throughout the brain hemispheres compared to animals without Chloro-DTG treatment.
Figure 13:
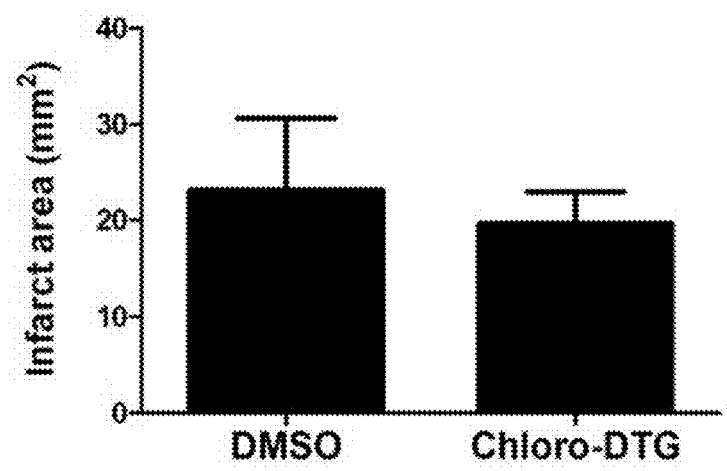
FIG. 13 is a graph showing the infarct volume in the stroke group receiving vehicle only versus Chloro-DTG treatment.

For the studies with other compounds based on the structure of DTG, twenty-four hours after MCAO, the rats began a sigma agonist treatment regimen. Vehicle or drug was prepared fresh each day. Testing procedures are summarized in FIG. 1. Daily subcutaneous injections (s.c) were administered daily for 3 days (ending 72 hours post-surgery) with either N,N'-di-p-Bromophenylguanidine hydrochloride (Bromo-DTG; 8.2 mg/kg/day), N,N'-di-m-Chlorophenylguanidine hydrochloride (Chloro-DTG; 8.5 mg/kg/day), N,N'-di-1-Naphthylguanidine hydrochloride (NAGH; 0.86 mg/kg/day), N,N'-di-p-nitrophenylguanidine HCL (NAD; 2.8 mg/kg), or vehicle. Animals received a total of 3 injections. The structures of the compounds are seen in FIG. 9.

For NAD testing, a total of 32 animals were randomly assigned into 2 groups: Vehicle (n=16), and rat treated with 2.8 mg/kg NAD (n=16). Vehicle consisted of 40% DMSO in sterile saline.

Behavioral Testing

After surgery, animals were tested was performed once before surgery and 30 days post-surgery for motor coordination and behavior. All behavioral data are reported as mean+sem.

Spontaneous Activity

Spontaneous Activity was measured during both the day (1 hr) and night (12 hrs) using an automated activity monitor (VersaMax, Accuscan Instruments, Inc). Spontaneous Activity was measured prior to stroke to establish the normal baseline for each individual animal as well as 1 month after the MCAO. The animals were placed in a Plexiglas box and allowed to roam freely. There is a three dimensional infrared array in this box and when a beam is broken, activity is recorded. A total of sixteen parameters were measured including: Vertical movement, Horizontal movement, and Stereotypic activity were selected for analysis: Horizontal activity (HA), Total distance travelled (TD), Number of movements (MVN), Movement time (MVT), Vertical activity (VA), Number of vertical movements (VMN), vertical time (VT), Stereotype counts (SC), Number of Stereotypy (SN), Stereotypy time (ST), Clockwise rotation (CR), counterclockwise rotation (CCR), Margin distance (MD), Marginal time (MT), Center distance (CD), and Center time (CT). The data are presented as mean+SEM of percent of baseline behavior.

Rotorod Test

Rotorod test, which measures motor coordination, was conducted using Omni-rotor Rotorod (Omnitech, Inc). Animals were trained on the accelerating rotorod apparatus for 3 consecutive days before times were collected. Animals were placed on the revolving rod and instrument was set to accelerate to a maximum speed of 40 rpm over 180 seconds. Latency to fall (in seconds) was recorded. This test was performed in triplicate once per day for 3 days.

Step Test

Rats were held tightly with one forelimb placed on a hard flat table top and then pulled for a length of 1 meter in the direction of the placed forelimb at constant velocity. The test was repeated with the opposite forelimb. This was repeated three times for each forelimb and the percent of contralateral forelimb paw was obtained. The bias was standardized as the absolute number of steps with the contralateral paw minus 100.

Elevated Body Swing Test

The animal was placed in a Plexiglas box (40×40×35.5 cm), allowed to habituate for 2 minutes and attain a neutral position, defined as having all four paws on the ground. The animal was held approximately 1 inch from the base of its tail and elevated to an inch above the Plexiglas cage surface. A swing was recorded whenever the animal moved its head out of the vertical axis to the right or left over 20 times. Swings were recorded using a hand counter. There is no bias when there are an equal number of swings to the left and right (i.e., 10 in each direction). The bias was standardized as the absolute value of the number of swings on the impaired side minus 10.

Passive Avoidance Test

On the first day of testing, animals were placed in the lighted chamber of a shuttlebox with a circular doorway opened to the darkened chamber. When the animals passed into the darkened chamber, they received a 0.9 mA foot shock for 2 second duration after which they were returned to their home cage. On day 2, foot shock was turned off and animals were placed into the same light chamber. The latency to enter the darkened chamber was recorded. The trial ended when the animal passed into the darkened side or 60 seconds had elapsed.

Cylinder Test

The animals were placed in a transparent cylinder about 20 cm in diameter and 30 cm in height with an open top. The number times each paw was placed on the sides of the cylinder was counted a 5 minute period. The test was videotaped and a mirror was placed behind the cylinder allowing the experimenter to see the placement of paws when the animal was facing away from the camera.

Corner Test

A 30 degree angle was formed using the edges of two plexiglass boards. The animals were placed halfway into the corner facing the corner and the total number of left and right turns was recorded. A total of 10 trials were conducted and videotaped. A non-lesioned animal turned randomly toward the left or right, while a lesioned animal preferentially turned toward the non-impaired (left) side. Results were reported as the percentage of ipsilateral (injury site, right side) versus contralateral turns.

Grip Test

Motor deficits were assessed using a grip strength meter (Bioseb, # BIO-GS3). The animals were held so the front left paw could firmly grasp the bar of the strength meter, and then pulled straight backward until its front paw released its grasp. Grip strength was recorded in Newtons (N). This test was repeated 3 times.

Histology and Immunochemistry

Tissue collection: Upon completion of the behavioral test at 30 days post MCAO, rats were euthanized with isoflurane and perfused transcardially with ice-cold phosphate buffer (PB) followed by 4% paraformaldehyde (PFA) in PB. Brains were carefully removed, post-fixed in 4% PFA for 24 hour, and equilibrated in 30% sucrose, and sectioned frozen in the coronal plane at 30 μm using a cryostat and cryopreserved at −20° C. for immunohistochemistry and histology.

Brain Infarction Quantification

Infarct size was determined by Nissl thionin staining. Six coronal sections were chosen from each animal representing 1 mm intervals from 1.7 mm anterior to bregma, to −3.3 mm posterior to bregma. Slides were washed in PBS and hydrated in a series of alcohols, then stained with Thionin to label Nissl bodies for 3 minutes. Slides were then dehydrated through a series of alcohols, cleared in Xylene, and coverslipped with DPX mountant (Electron Microscopy Sciences, Ft. Washington, Pa.). Photographs of the sections were taken on an Olympus IX71 microscope with DP manager software (Olympus America Inc., Melville, N.Y.) at 1.25×. Infarct size was determined with the indirect method. We measured the ipsilateral healthy (intact) tissue and the area of the contralateral hemisphere a using ImageJ software. The infarct area was obtained by deducting the ipsilateral volume from the total contralateral volume and was expressed as percent of contralateral hemisphere.

Evaluation of White Matter Injury

To evaluate white matter injury, coronal brain sections from each the animals were stained with Luxol Fast Blue (LFB; Sigma-Aldrich). For Luxol Fast Blue (LFB) staining, slides were dehydrated in 95% ethanol and incubated in LFB solution at 56° C. overnight. The following day slides were rinsed in 95% ethanol and distilled water and differentiated in 0.1% lithium carbonate solution for 20 s followed by 70% ethyl alcohol for 30 s, and finally rinsed in distilled water. After complete gray and white matter differentiation, slides were dehydrated and placed under coverslips with DPX. The quantitative analysis for demyelination in LFB staining section was performed as described previously with some modification (Virgili, Espinosa-Parrilla et al. 2011; Yu, Gong et al. 2012). LFB stained area was measured on the randomly selected sections (n=21-23 animals/group) to assess demyelination. The extent of the LFB positive area was quantified using a pixel grayscale approach in ImageJ software (National Institute of Health, USA). Briefly, images were converted into a gray scale format and a contour was drawn around each individual hemisphere. The threshold was set for LFB-positive area by determining the maximum threshold of corpus callosum as "highest gray value". Once calibrated, the amount of LFB staining was measured as the percentage of hemispheric area using ImageJ software.

Immunohistochemistry

Anti-Iba1 (1:500; Wako 019-19741) immunocytochemistry was used for the specific identification of microglia. The slide was rinsed in PBS, quenched for peroxidase using 1% $H_2O_2$ in methanol for 15 minutes, and incubated overnight at 40 C with primary antibody. The slides were then incubated with biotinylated secondary antibody (1:200 goat anti-rabbit; Vector Labs BA-1000) for 1 hour at room temperature, followed by avidin bound peroxidase complex (ABC-kit, Vector) for 1 hour. Following several washes in PBS, slides were treated with 3-3'diaminobenzidine tetrahydrochloride (DAB) for about 3 to 5 minutes (Pierce, PI 34065). The development of the color reaction was stopped by washing with PBS. Slides were then dehydrated and coverslipped. Iba-1 positive cells were quantified (n=12) as previously detailed by Smirkin et al. (Smirkin, Matsumoto et al. 2010) with little modification. Four images (Upper lateral/medial and lower lateral/medial) in the region around the ischemic core in the ipsilateral hemisphere and the corresponding fields from the contralateral hemisphere were captured using an Olympus IX71 microscope at 20× objective with DP manager software. Total number of Iba-1 positive cells were counted manually by two observer using ImagePro plus software.

Statistical Analysis

Data are expressed as group mean±SEM and were analyzed using GraphPad Prism 5.01 software (GraphPad Software, San Diego, Calif.). All analyses were performed using a Student's t-test. A value of $p<0.05$ was considered significant for all analyses.

Results for NAGH:

NAGH Improves Vertical activity

Daytime Spontaneous Activity: Spontaneous activity was measured prior to MCAO and NAGH treatment and then 1 month post MCAO and NAGH treatment. Daytime spontaneous activity was measured at 5-min intervals over a 1-hr test period. When daytime spontaneous activity was examined for differences between the DMSO group and the NAGH-treated groups, the overall analyses showed that the NAGH-treated animals were less active on all measured parameters except for VMN, CCR, CD, and CT (Data not shown). All vertical movement parameters (VA, VMN, VT) significantly correlate with the infarct volume, while most of horizontal movement parameters except the distance travelled in the margin, did not correlate with the infarct volume (Shen and Wang 2010). These researchers also did not find any correlation between the size of infarction and all stereotypy parameters (SC, SN, and ST).

Figure 2:
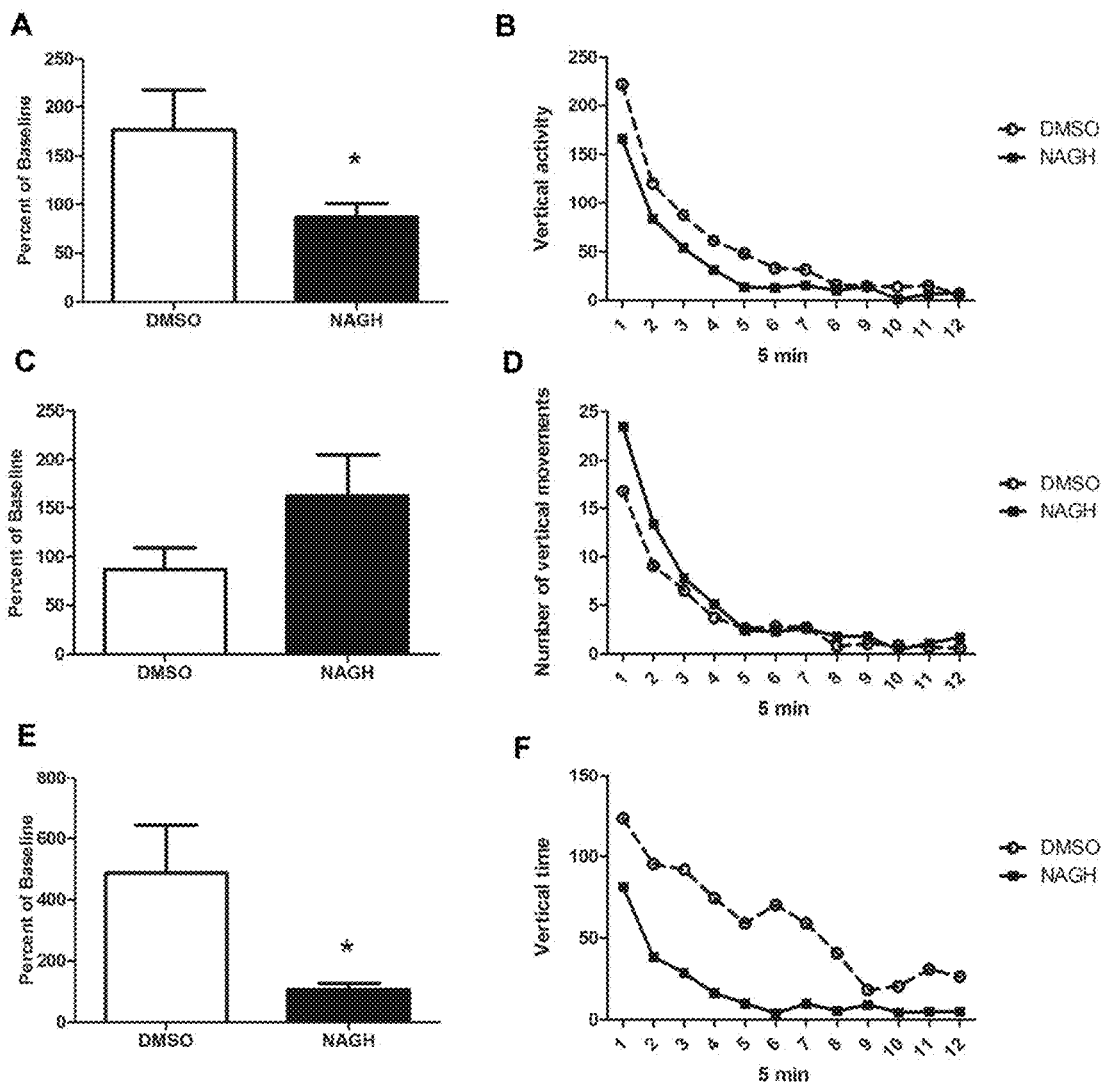
FIG. 2 is a series of images depicting comparison of daytime vertical movement with or without NAGH treatment at 1 month. Percent baseline of three parameters of vertical movement i.e. VA (A), VMN (C), and VT (E) during the daytime testing period at 1 month post-treatment. Time course of these parameters over the entire 1-hr test at 1 month post-treatment (B, D, and F respectively). Note that activity decreases steadily over the first four observation periods and then remains relatively stable for the remainder of the test.

When the inventors analyzed the three parameters of vertical movement, i.e. VA, VMN, and VT, significant differences were found between the groups on VA and VT but not VMN ($p>0.05$); the animals in the NAGH treatment group were significantly less active on VA ($p=0.03$) and VT ($p=0.01$) (FIG. 2). However, the NAGH treatment group was more active than DMSO group on VMN ($p=0.15$). The overall horizontal activities during daytime were similar and there were no significant differences between the animals that received NAGH and DMSO group. Although there was a decrease in activity in animals treated with NAGH across each parameter of stereotypy activity (i.e. SC, SN, and ST) these failed to reach a statistically significant level ($p>0.05$).

Figure 3:
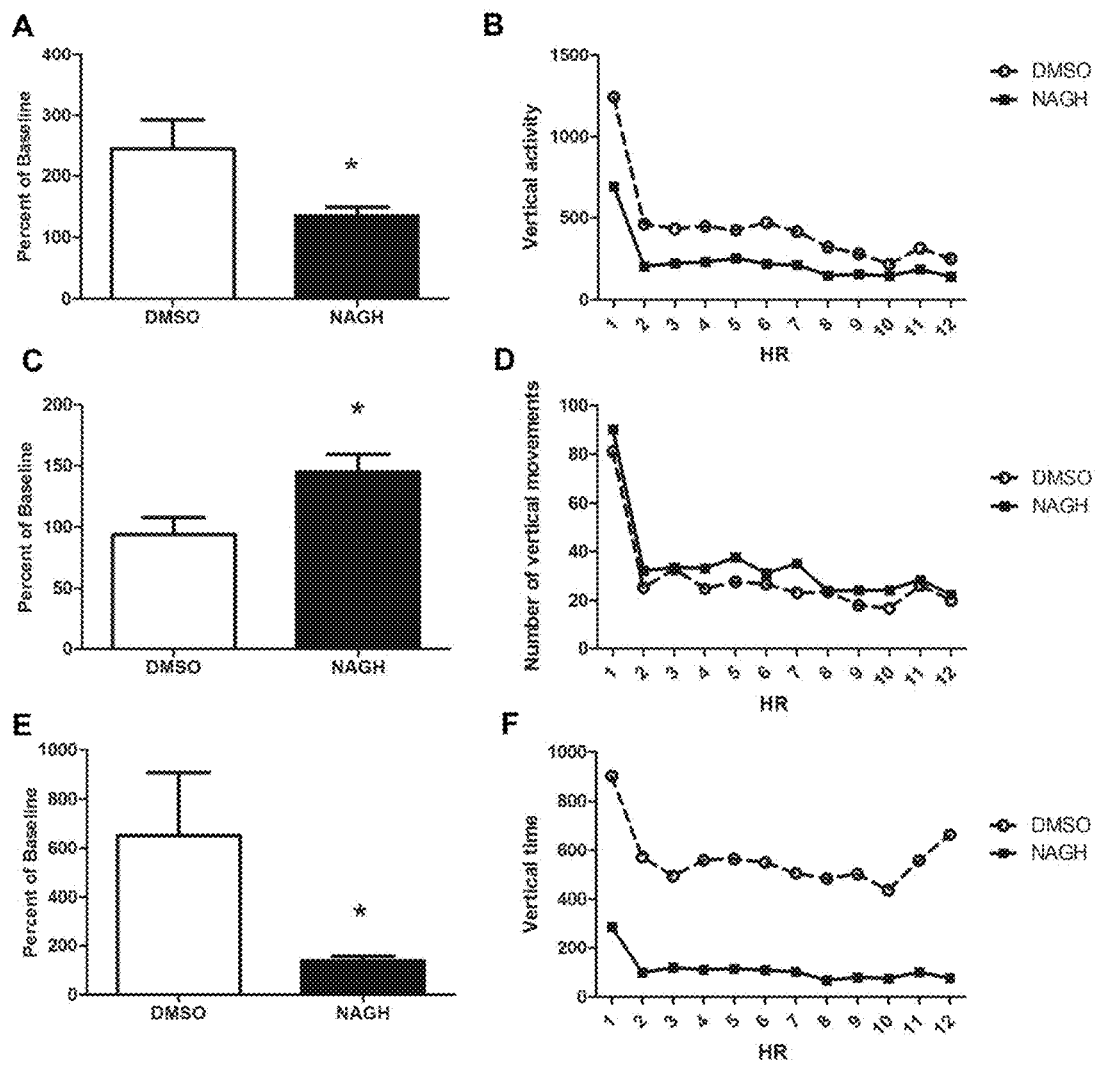
FIG. 3 is a series of images depicting comparison of Nighttime vertical movement with or without NAGH treatment at 1 month. Percent baseline of three parameters of vertical movement i.e. VA (A), VMN (C), and VT (E) during the Nighttime testing period at 1 month post-treatment. Time course of these parameters over the entire 12-hr test at 1 month post-treatment (B, D, and F respectively). The same pattern of decreasing activity was also observed at this time.

Nighttime Spontaneous Activity: Nighttime spontaneous activity was measured at 1-hr intervals over a 12-hr test period. Overall pattern of behavior during nighttime was similar to that observed during the day, i.e. there was less activity observed in animals treated with NAGH on all measured parameters than the DMSO group except for VMN (Data not shown). Further, there was a significant difference on all measured vertical movement parameters between the groups (FIG. 3). The animals in the NAGH treatment group were significantly less active on VA (p=0.01), and VT (p=0.03) and significantly more active on VMN (p=0.015). Although there was a decrease in activity in animals treated with NAGH across each horizontal parameters monitored, these changes did not reach statistical significance. All parameters of stereotypic behavior (SC, SN, and ST) did not show any significant difference between groups.

NAGH Improves Body Asymmetry

Figure 4:
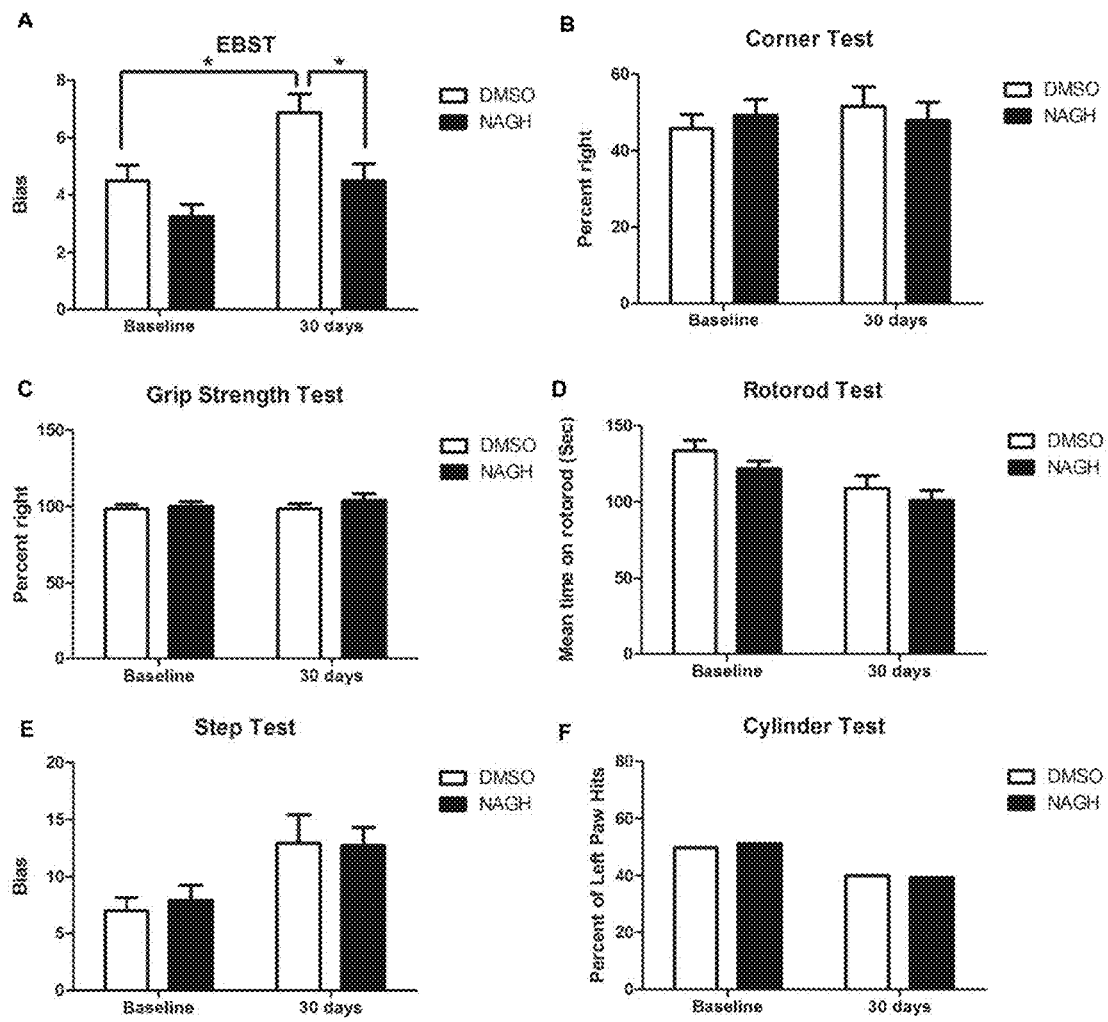
FIG. 4 is a series of images depicting the results of the behavioral tests including Elevated body swing test (A), Corner test (B), Grip strength test (C), Rotarod test (D), Step test (E), and fore limb use asymmetry (cylinder test) (F) Step test at baseline and at 30 days after MCAO. Values are mean±SEM, n=27 to 28. *p<0.05 Vs control.

A battery of behavioral tests was performed to determine the effects of NAGH on behavioral outcome following MCAO. The overall behavioral data showed there were no significant differences between the NAGH group and the vehicle group on all tests except on EBST which is a measure of motor asymmetry (FIG. 4). On EBST, there was no significant difference in the bias between the animals treated with NAGH at baseline and those treated with DMSO (p=0.073). However, at 30 days the animals treated with NAGH showed significantly less bias (p=0.009) compared to DMSO group.

NAGH Failed to Significantly Reduce Infarct Volume

Figure 5:
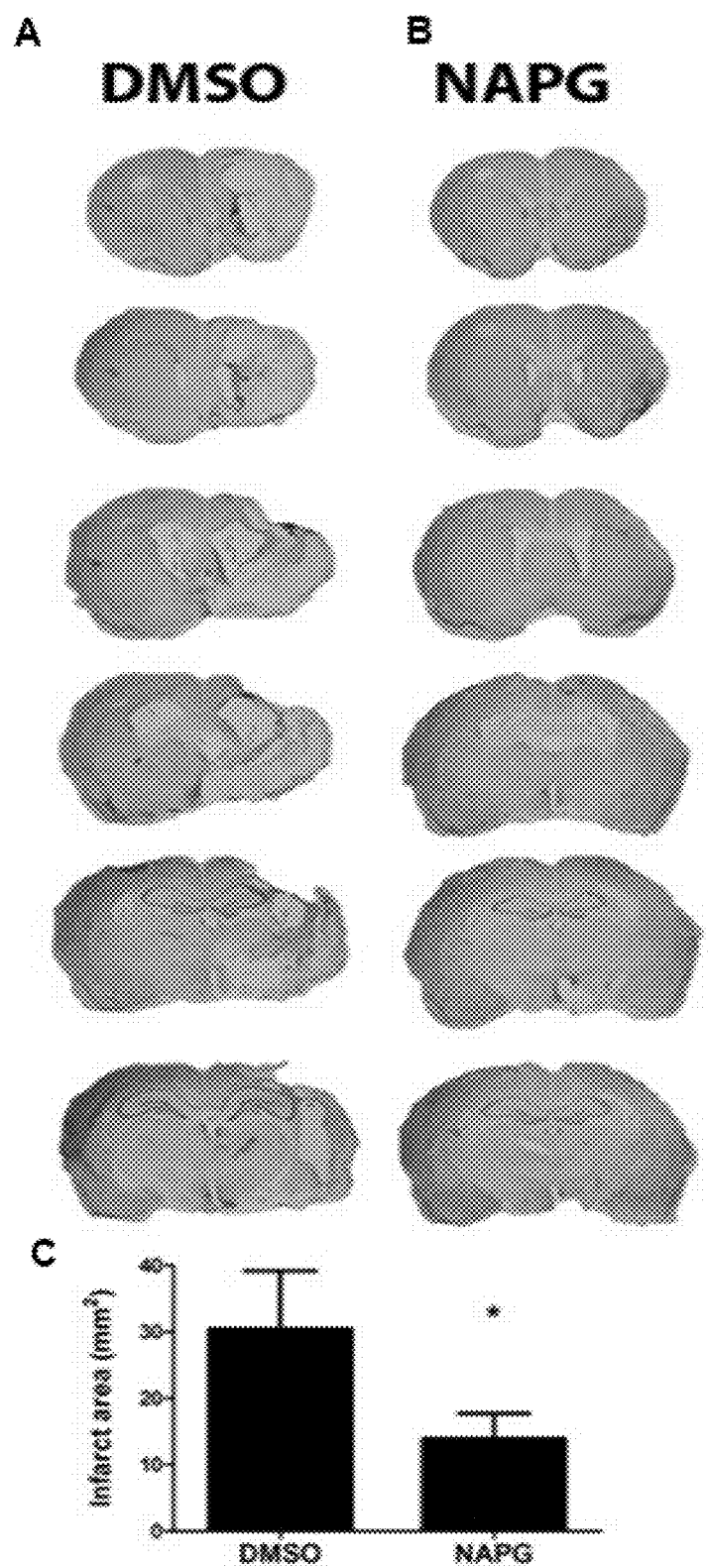
FIG. 5 is a series of images depicting Nissl-Thionin stained coronal brain sections. Nissl-Thionin staining was used to determine infarct volumes of rats following MCAO treated with DMSO (A) or NAGH (B). Infarct size was determined at 6 pre-determined levels beginning 1.7 mm anterior to bregma to 3.3 mm posterior to bregma at 1 mm intervals. The area (mm2) of intact tissue in the ischemic and normal hemispheres was measured using Image Pro Plus. The relative infarct volume was determined as the difference between the sum of the normal hemisphere and the sum of the infarcted hemisphere divided by the sum of the normal hemisphere multiplied by 100. Lesion size in the infarcted hemisphere of the NAPG treated animals was significantly smaller than lesion sized in the DMSO treated group (*p<0.05) NAGH failed to decrease infarct volume compared to the MCAO only group. (C) Percent contralateral infarct area of animals treated with NAGH and DMSO. Values are mean±SEM, n=27-28 p>0.05

Ischemic damage was determined by total infarct size using Nissl-Thionin staining. Although there was reduced thionin staining in the ipsilateral corpus striatum and cortical area animals treated with DMSO (FIG. 5A) than that of NAGH treated animals (FIG. 5B), the difference did not reach statistical significance (p=0.86). Infarct volume in the stroke group receiving vehicle only (n=25) was 17.57±4.4.3%, whereas animals receiving NAGH (n=27) showed infarcts involving only 13.58±2.3% of the hemisphere (FIG. 5C).

NAGH Exerts its Neuroprotective Effects via Preservation of White Matter Tracts

To determine treatment effects of NAGH on myelinating oligodendrocytes in the rat brain following MCAO, the inventors histologically stained white matter tracts with Luxol Fast Blue. After MCAO, the demyelination in the DMSO treated group (n=23) showed a statistically significant reduction in LFB staining in the ischemic hemisphere (9.13±0.5%) compared to non-infarcted hemisphere (11.4±0.49%, p<0.05) that persisted at 30 days post-stroke (FIG. 6A, B, E). In animals receiving NAGH (n=22), myelinated fibers were intensely stained by LFB in the striatum and cortex. The levels of LFB did not change between the ischemic and non-ischemic hemisphere 10.32±0.48% and 9.81±0.38% respectively (p>0.05), suggesting white matter tracts were more intact in treated animals (FIG. 6C, D, E). Indeed, the percent change in LFB staining from contralateral to ipsilateral hemisphere is 18+5.6% in the DMSO treated group compared to −0.73+7.7% in the NAGH treated group (p<0.05). These results demonstrated severe and long-term white matter demyelination following MCAO.

NAGH Reduces Iba1 Positive Cells in the Infarcted Regions

Figure 7:
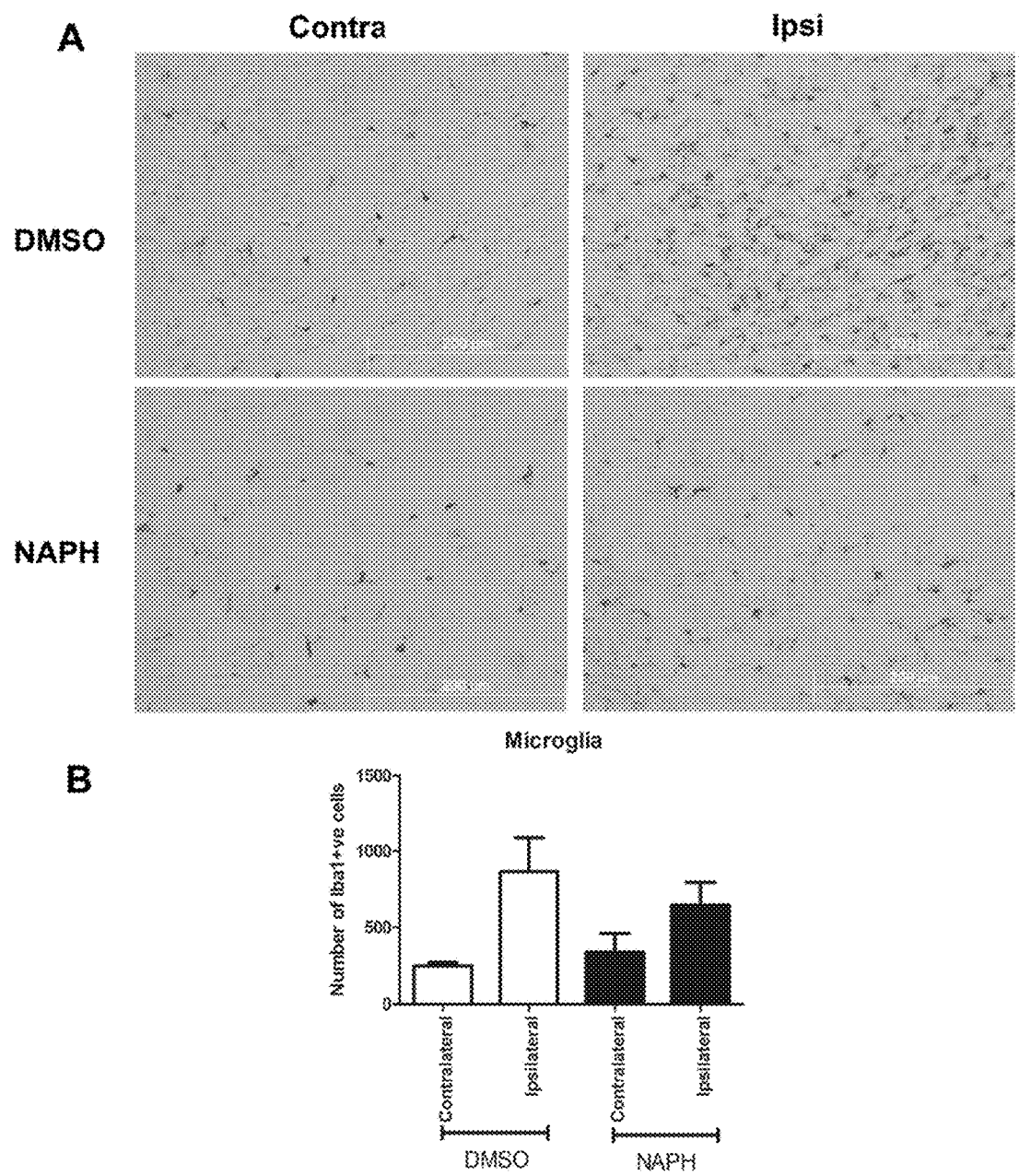
FIG. 7 is a series of images depicting Iba1 Immunostaining of rat brains 30 days after MCAO. (A) Representative Iba1 staining brain from DMSO and NAGH treated rats after MCAO. NAGH treated brains showed decreased number of activated microglia in the ipsilateral hemisphere (B). Values are mean±SE. p>0.05

To test whether NAGH alters activation of immune cells in the brain following MCAO, Iba1 expression was measured in the ischemic brain since Iba1 labels microglia regardless of their activation state. In general, there are more intensely stained amoeboid or round shaped cells in the peri-infarct and ischemic core following MCAO, suggesting that these immunopositive cells were activated microglia (FIG. 7). Iba1 positive cells were mostly located in the cortex, striatum, and adjacent to the lateral ventricle. The observations demonstrate that the peri-infarct and ischemic core of DMSO treated rats contain more activated microglia than the NAGH treated animals even 30 days after stroke, although the difference was not statistically significant (p>0.05).

NAGH blocks microglial migration via actions at both σ-1 and σ-2 receptors.

Figure 8:
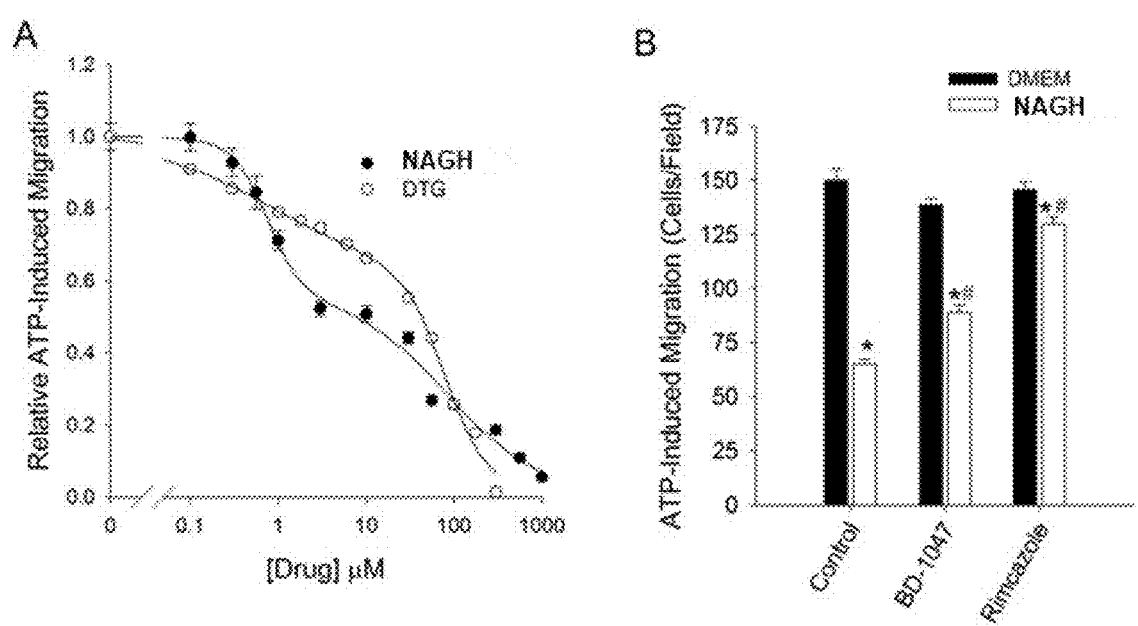
FIG. 8 is a series of images confirming NAGH acts as a sigma receptor agonist. A) Concentration-response relationship for NAGH (closed circles) and DTG (open circles) inhibition of microglial migration evoked by 100 μM ATP. Solid line represents best fit to the NAGH data using a two-component Langmuir-Hill equation with the Emax, IC50 and Hill coefficient being 0.43, 0.75 μM and 2.2 for the high affinity component and 0.57, 84 μM and 0.80 for the low affinity component, respectively. Dashed line represents best fit to the DTG data using a two-component Langmuir-Hill equation with the Emax, IC50 and Hill coefficient being 0.38, 0.76 μM, and 0.59 for the high affinity component and 0.62, 80 μM, and 1.7 for the low affinity component, respectively. Points represent mean (±SEM) and for all points, n>9. B) Bar graph of the mean (±SEM) number of microglial cells migrating in response to 100 µM ATP when ATP was added alone (DMEM) or in the presence of 100 µM NAGH. Microglia were further exposed to no σ antagonist (Control), or the σ-1 antagonist, BD-1047 (10 µM, BD-1047), or the σ-2 antagonist, rimcazole (10 µM, Rimcazole). Asterisks denote significant difference between DMEM and NAGH within Control, BD-1047 and Rimcazole groups, respectively. Pound symbols indicate significant difference between Control, BD-1047 and Rimcazole within DMEM and NAGH groups, respectively. P<0.05 and n=24 for all groups.

FIG. 8A illustrates the concentration-response relationship for NAGH (closed circles) and DTG (open circles) inhibition of microglial migration evoked by 100 μM ATP. Solid line represents best fit to the NAGH data using a two-component Langmuir-Hill equation with the Emax, 1050 and Hill coefficient being 0.43, 0.75 μM and 2.2 for the high affinity component and 0.57, 84 μM and 0.80 for the low affinity component, respectively. Dashed line represents best fit to the DTG data using a two-component Langmuir-Hill equation with the Emax, 1050 and Hill coefficient being 0.38, 0.76 μM, and 0.59 for the high affinity component and 0.62, 80 μM, and 1.7 for the low affinity component, respectively. Points represent mean (±SEM) and for all points, n>9. FIG. 8B depicts a bar graph of the mean (±SEM) number of microglial cells migrating in response to 100 μM ATP when ATP was added alone (DMEM) or in the presence of 100 μM NAGH. Microglia were further exposed to no σ antagonist (Control), or the σ-1 antagonist, BD-1047 (10 μM, BD-1047), or the σ-2 antagonist, rimcazole (10 μM, Rimcazole). Asterisks denote significant difference between DMEM and NAGH within Control, BD-1047 and Rimcazole groups, respectively. Pound symbols indicate significant difference between Control, BD-1047 and Rimcazole within DMEM and NAGH groups, respectively. P<0.05 and n=24 for all groups.

Results for Other Sigma Agonists

With regard to the other sigma agonists, they were also tested to determine if they would induce long-term recovery of function and minimize lesion size in the brain when administered 24-72 hours after MCAO. While DTG induces short-term improvements in neurohistological outcome (Hall A A, Leonardo C C, Collier L A, Rowe D D, Willing A E, Pennypacker K R. Neurosci. 2009; 164:470-477), the therapeutic efficacy of this sigma receptor agonist is minimal because the early benefits are not maintained long term (Leonardo, C. C., A. A. Hall, et al. (2010). Transl Stroke Res 1(2): 135-145).

Figure 14:
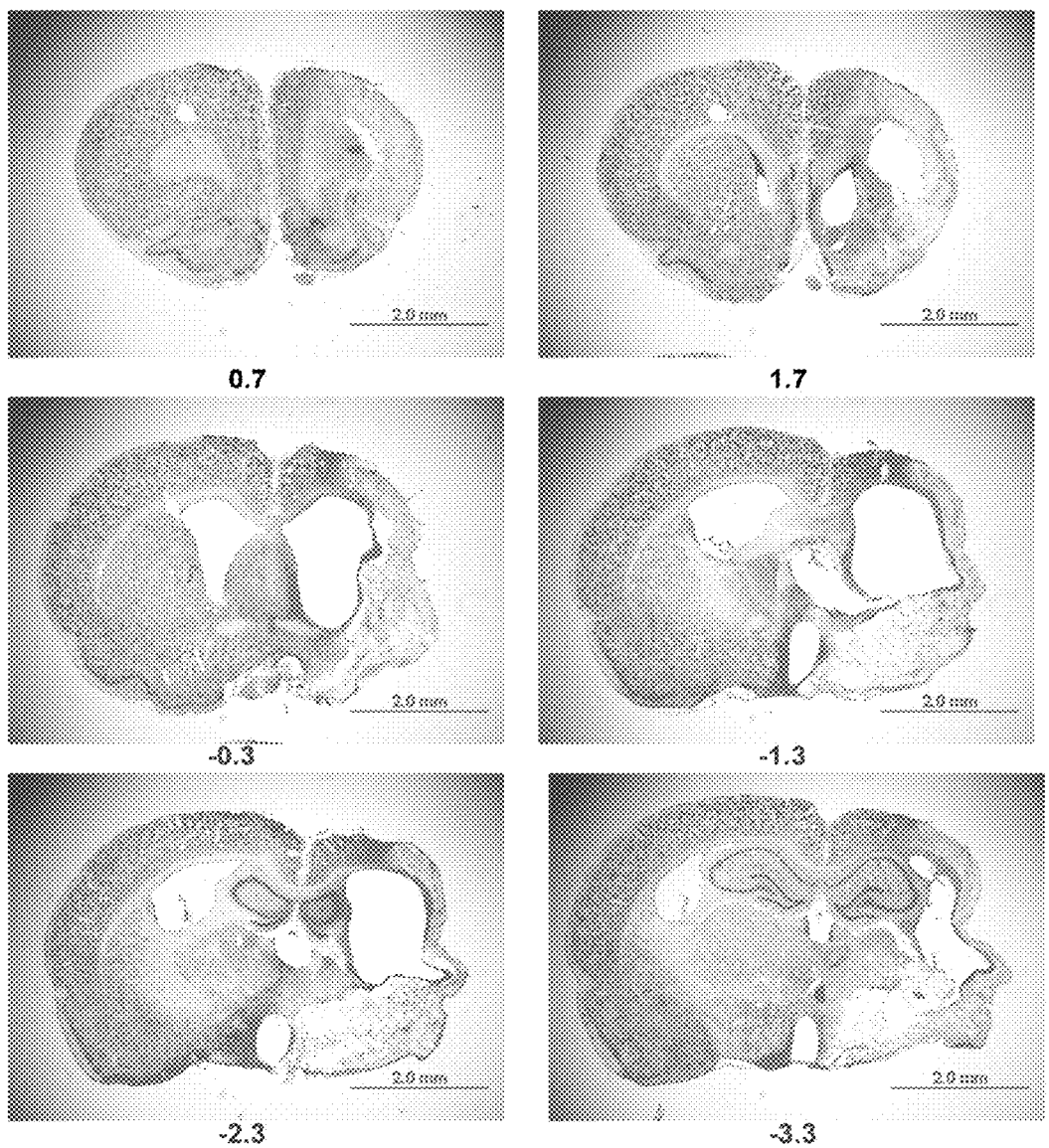
FIG. 14 is an image showing results of MCAO on Thionin staining throughout the brain hemispheres in animals without NAD treatment thionin staining.
Figure 15:
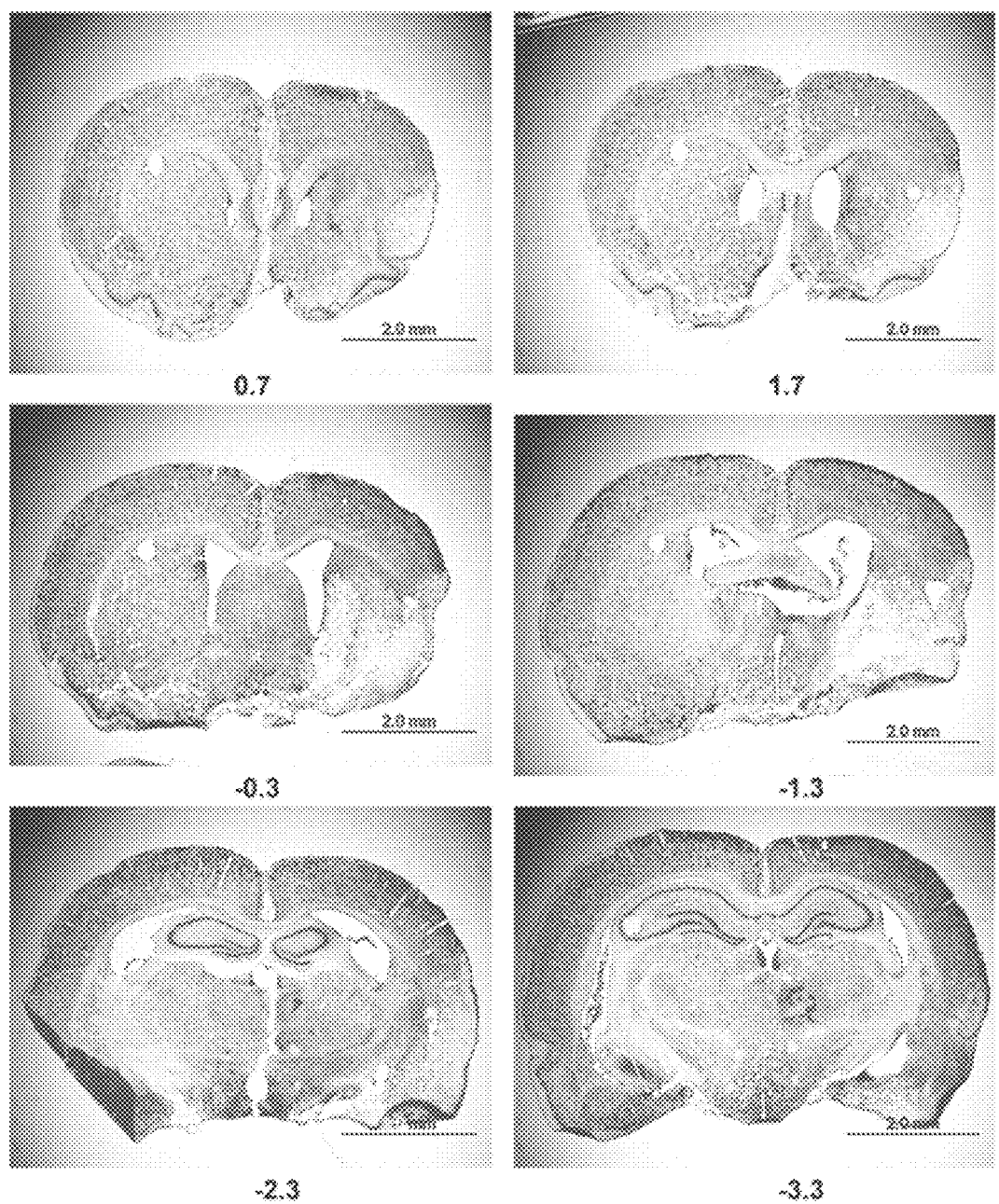
FIG. 15 is an image showing treatment with NAD resulted in prominent Thionin staining throughout the brain hemispheres whereas animals without NAD treatment thionin staining was preserved mostly in the contralateral hemisphere.
Figure 16:
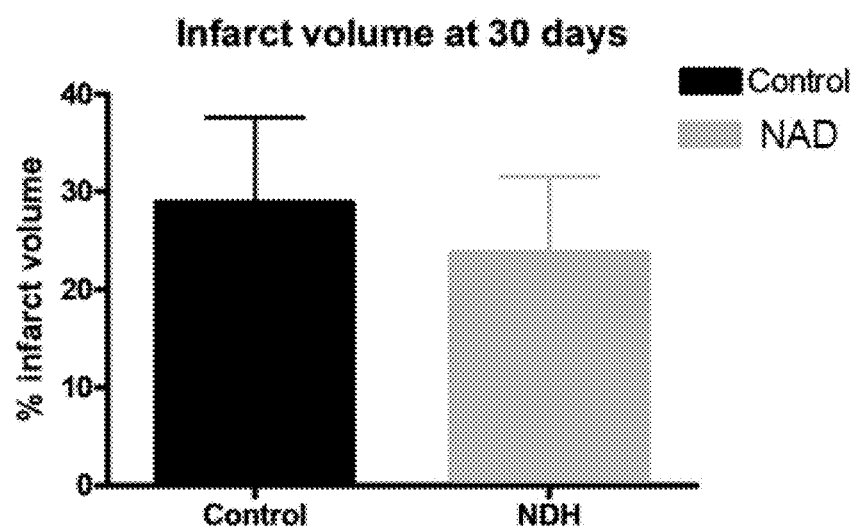
FIG. 16 is a graph showing the infarct volume in the stroke group receiving vehicle only (n=8) was 30.49±8.71%, whereas animals receiving NAD (n=8) showed infarcts involving only 13.93±3.79% of the hemisphere.
Figure 17:
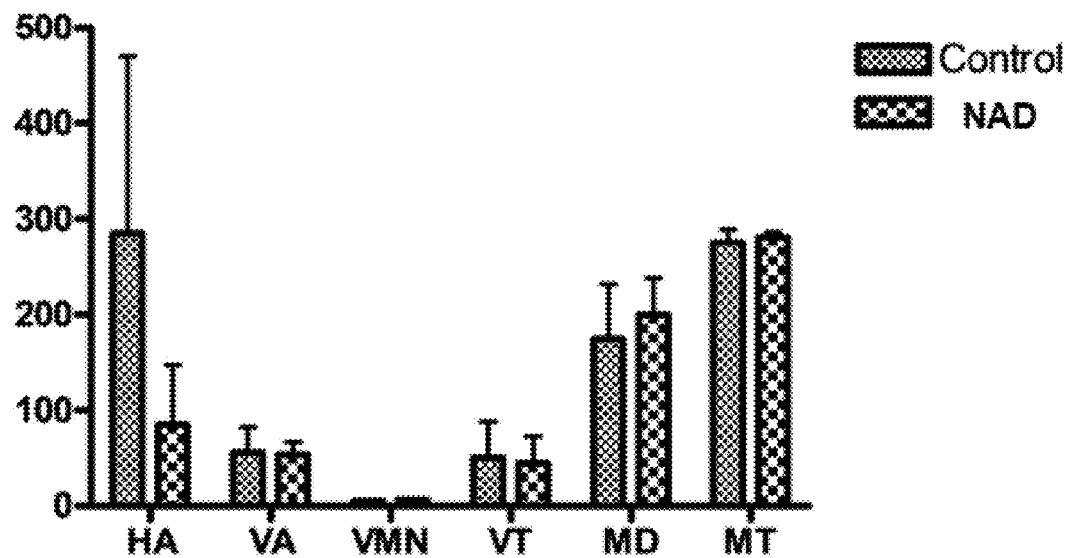
FIG. 17 is a graph showing overall animals treated with NAD were less active then the non-treated animals at 30 days after MCAO. Day time activity at 1 month post MCAO.
Figure 18:
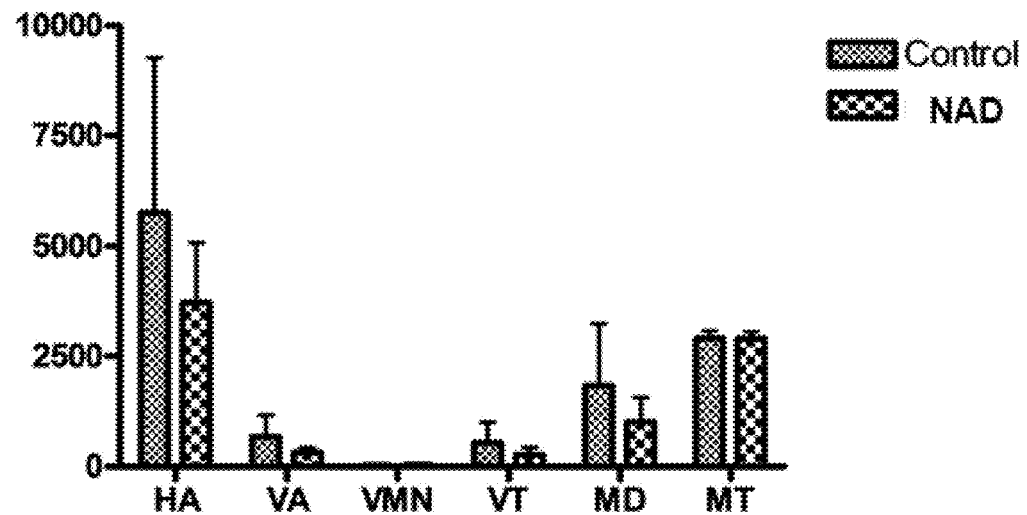
FIG. 18 is a graph showing overall animals treated with NAD were less active then the non-treated animals at 30 days after MCAO. Nighttime time activity at 1 month post MCAO.
Figure 19:
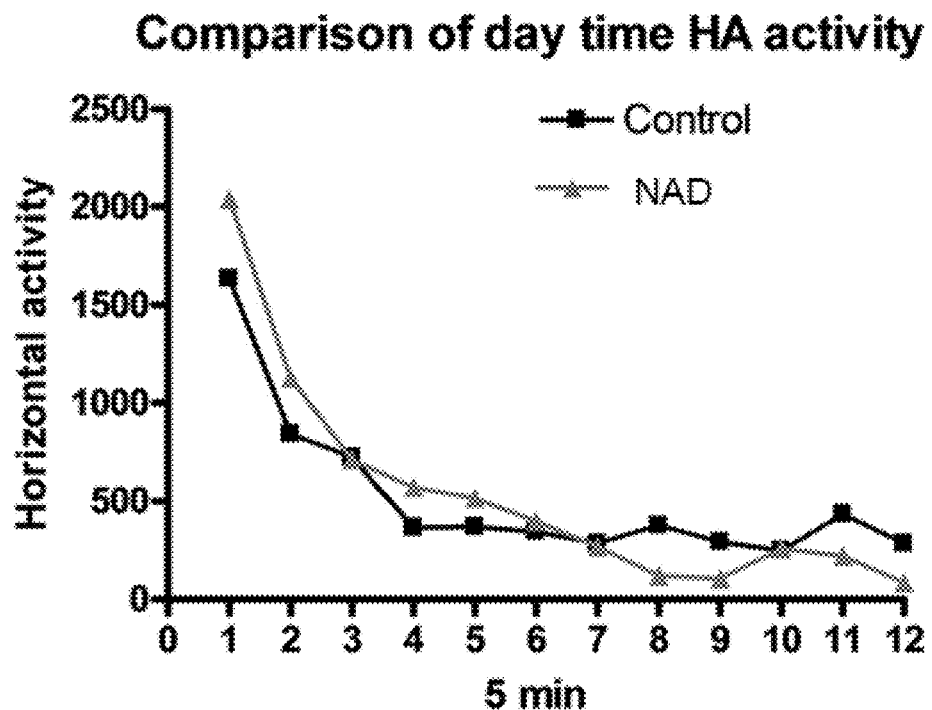
FIG. 19 is a graph showing overall animals treated with NAD were less active then the non-treated animals at 30 days after MCAO. Horizontal activity during the day time testing period.
Figure 20:
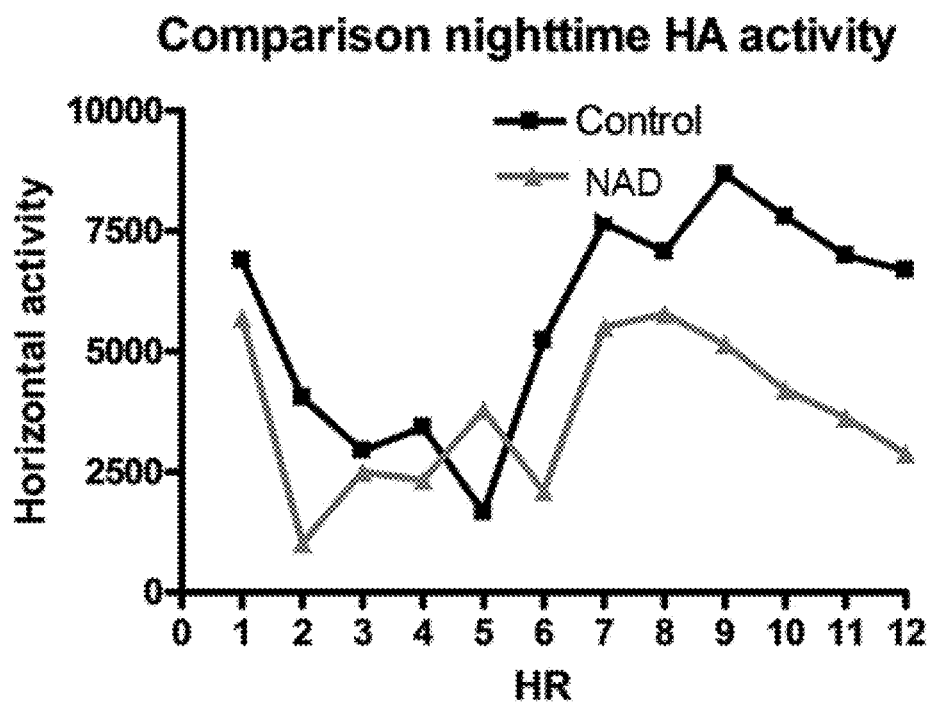
FIG. 20 is a graph showing overall animals treated with NAD were less active then the non-treated animals at 30 days after MCAO. Horizontal activity during the nighttime testing period.
Figure 21:
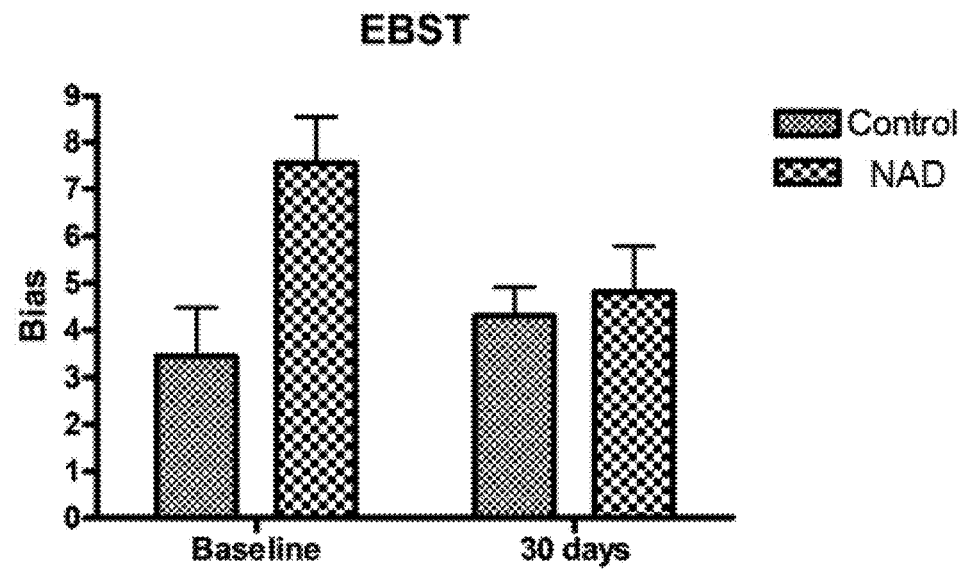
FIG. 21 is a graph showing the elevated body swing test at baseline and at 30 days after MCAO comparing control animals and those receiving NAD. Values are mean±SEM, n=9 to 12. *p<0.05 Vs control.

Results from Bromo-DTG and Chloro-DTG did not show significant effects over vehicle, as seen in FIGS. 10 through 13. With NAD, there was a tendency for infarct volume of treated animals to decrease, as seen in FIGS. 14 and 15, but this was not significant (23.78±7.78% compared to 28.84±8.78% in MCAO only group, as seen in FIG. 16. Behaviorally, animals treated with NAD showed less activity than MCAO-only animals, as seen in FIGS. 17 through 20.

The overall behavioral data showed there was no significant difference between the NAD and vehicle treated groups except on the Grip Strength test and Step test, as seen in FIGS. 21 through 28. The average grip strength of NAD treated animals was significantly higher than that of non-treated rats (p=0.0007). Similarly, on the step test, the untreated animals took fewer steps with their impaired paw compared to their unimpaired paw (86.7+6.2%) at 30 days post-stroke, while NAD treated animals showed no decrement (100.3+5.6%, p<0.05).

Further analysis is needed to determine the extent of the behavioral recovery and determine if it is related to increased neuronal survival (infarct size), preservation of oligodendrocytes and white matter tracts or modulation of post-stroke inflammation (microglia and astrocytes).

Figure 22:
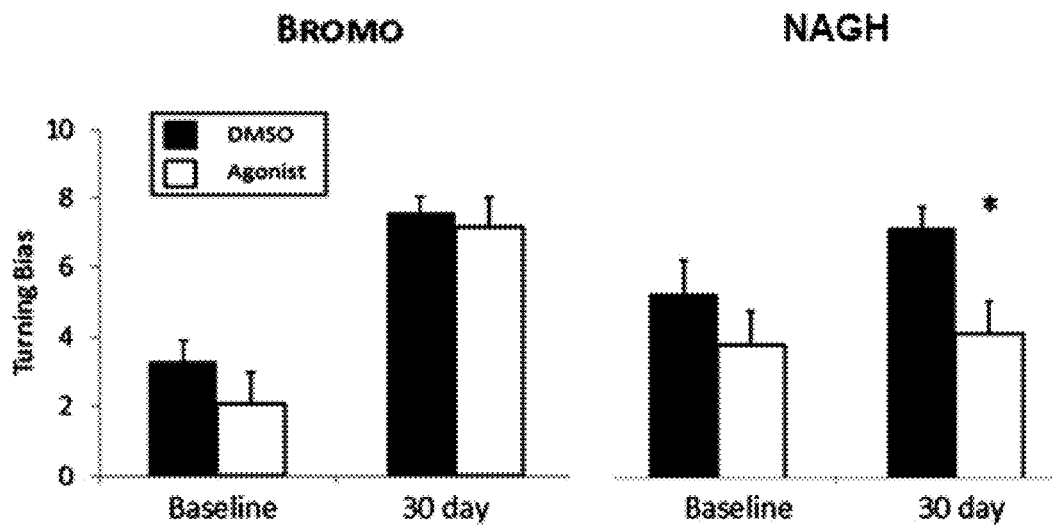
FIG. 22 is a graph showing the elevated body swing test at baseline and at 30 days after MCAO comparing controls against Bromo-DTG or NAGH.
Figure 23:
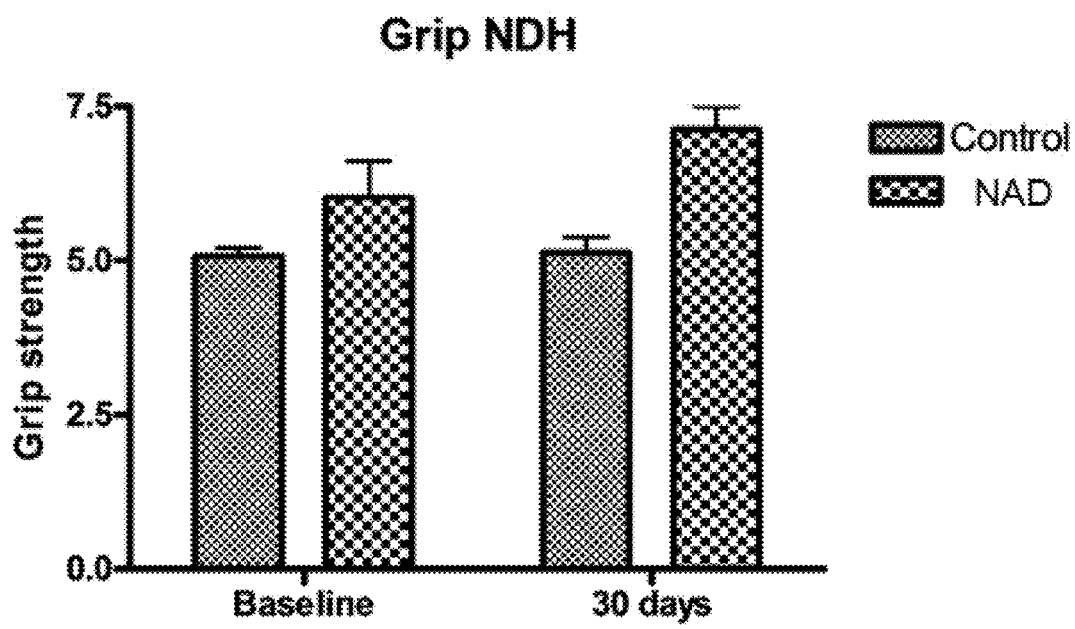
FIG. 23 is a graph showing the grip strength test comparing control versus NAD. Values are mean±SEM, n=9 to 12. *p<0.05 Vs control.
Figure 24:
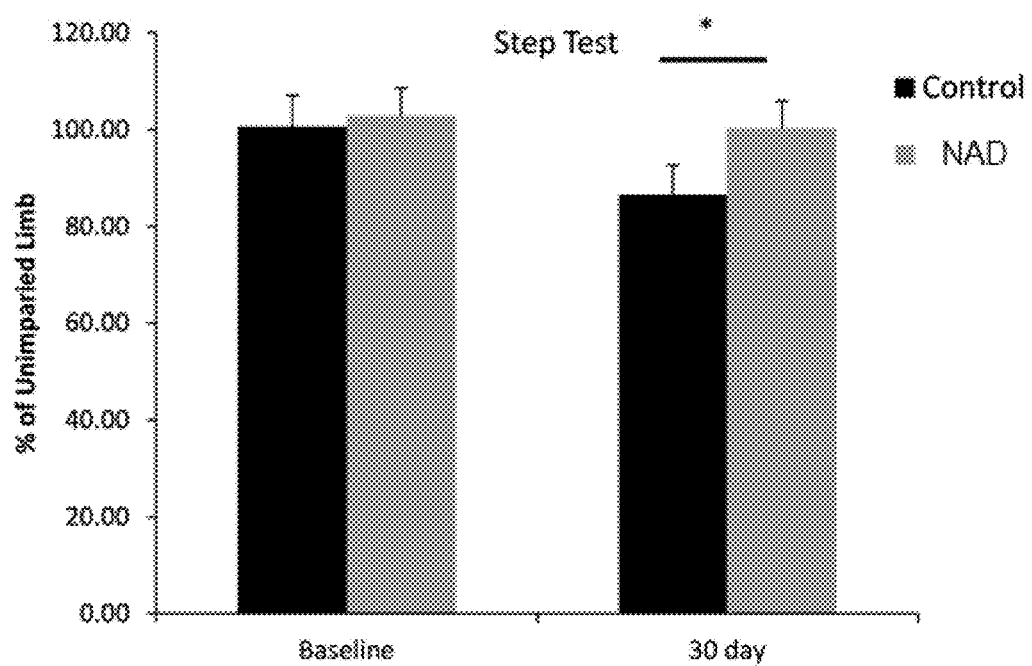
FIG. 24 is a graph showing the step test at baseline and at 30 days after MCAO for control versus NAD. Values are mean±SEM, n=9 to 12. *p<0.05 Vs control.
Figure 25:
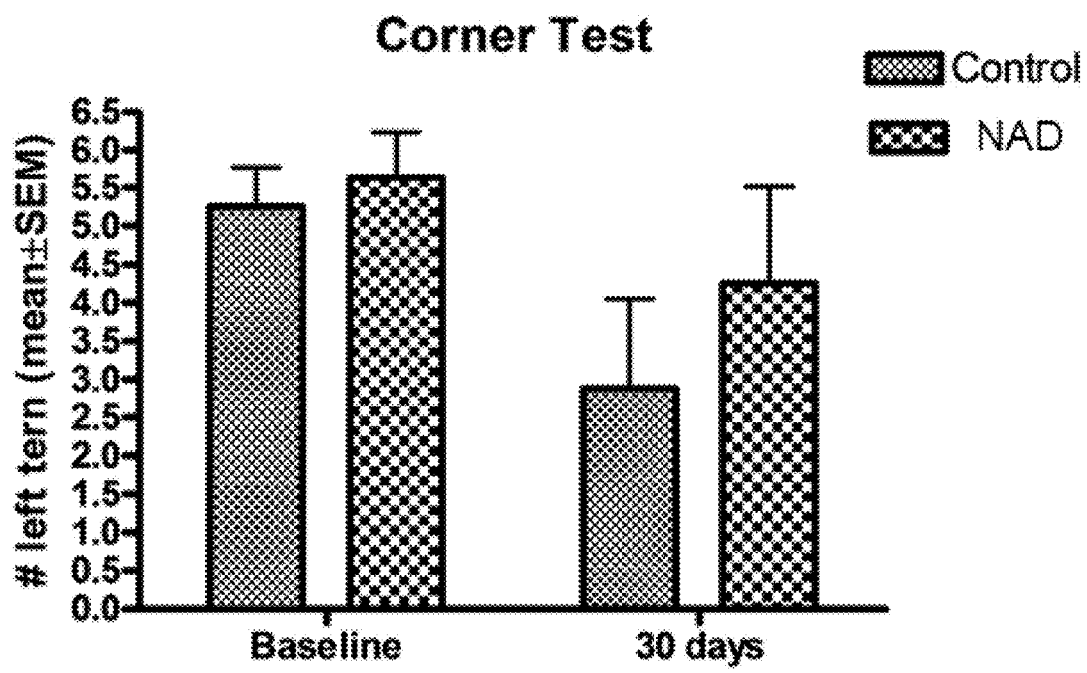
FIG. 25 is a graph showing the corner test at baseline and at 30 days after MCAO for control versus NAD. Values are mean±SEM, n=9 to 12. *p<0.05 Vs control
Figure 26:
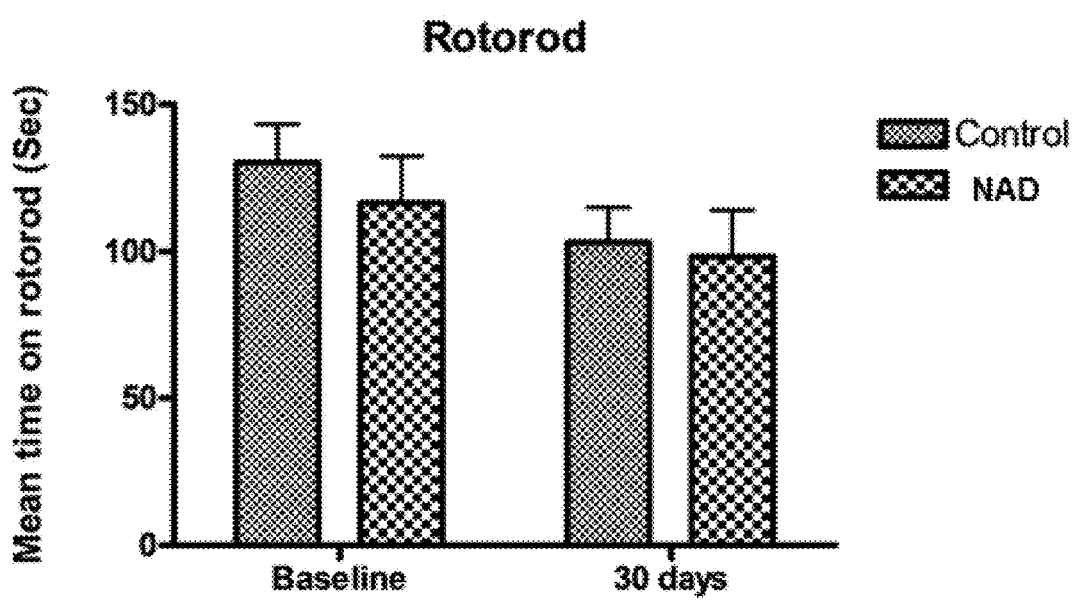
FIG. 26 is a graph showing the rotorod test at baseline and at 30 days after MCAO for control versus NAD. Values are mean±SEM, n=9 to 12. *p<0.05 Vs control
Figure 27:
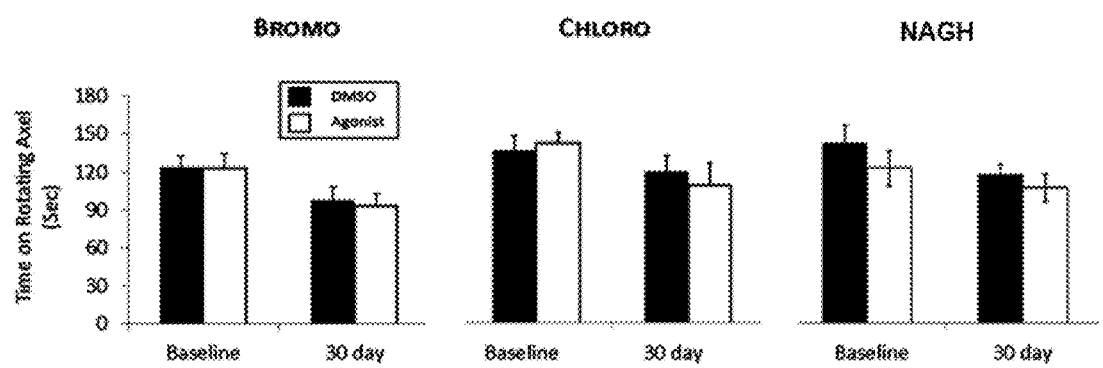
FIG. 27 is a graph showing the rotorod test at baseline and at 30 days after MCAO comparing control versus Bromo-DTG, Chloro-DTG or NAGH.
Figure 28:
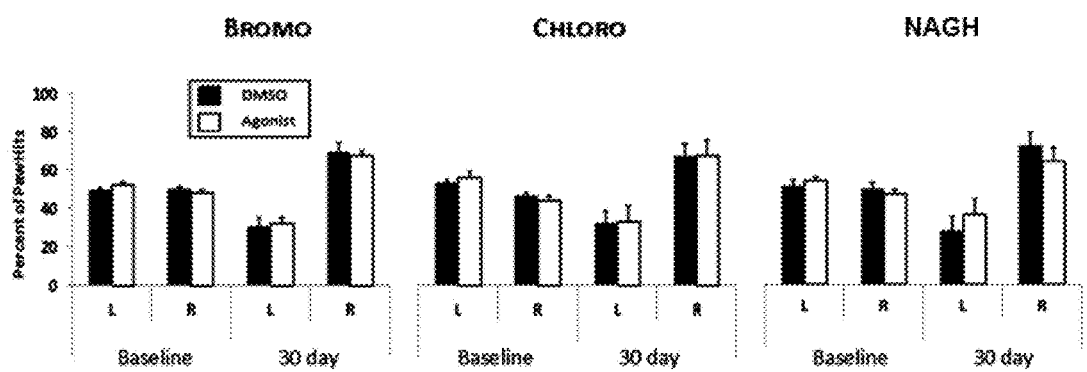
FIG. 28 is a graph showing the cylinder test at baseline and at 30 days after MCAO comparing control versus Bromo-DTG, Chloro-DTG or NAGH.

In conclusion, examining the available data gathering from testing each compound, the NAGH agonist was found to be the only sigma receptor agonist in the test group that reduced infarct volume and increased functional recovery, as seen in FIGS. 22, 27, 28. The NAGH treated rats had significantly less motor asymmetry than vehicle treated rats (*p<0.05). On the cylinder test, the number of paw hits on the side of the cage decreased dramatically for both paws (data not shown), but the extent of the decrease was larger for the left (contralateral) paw. However, changes in asymmetry on the cylinder test failed to gain significance.

Figure 6:
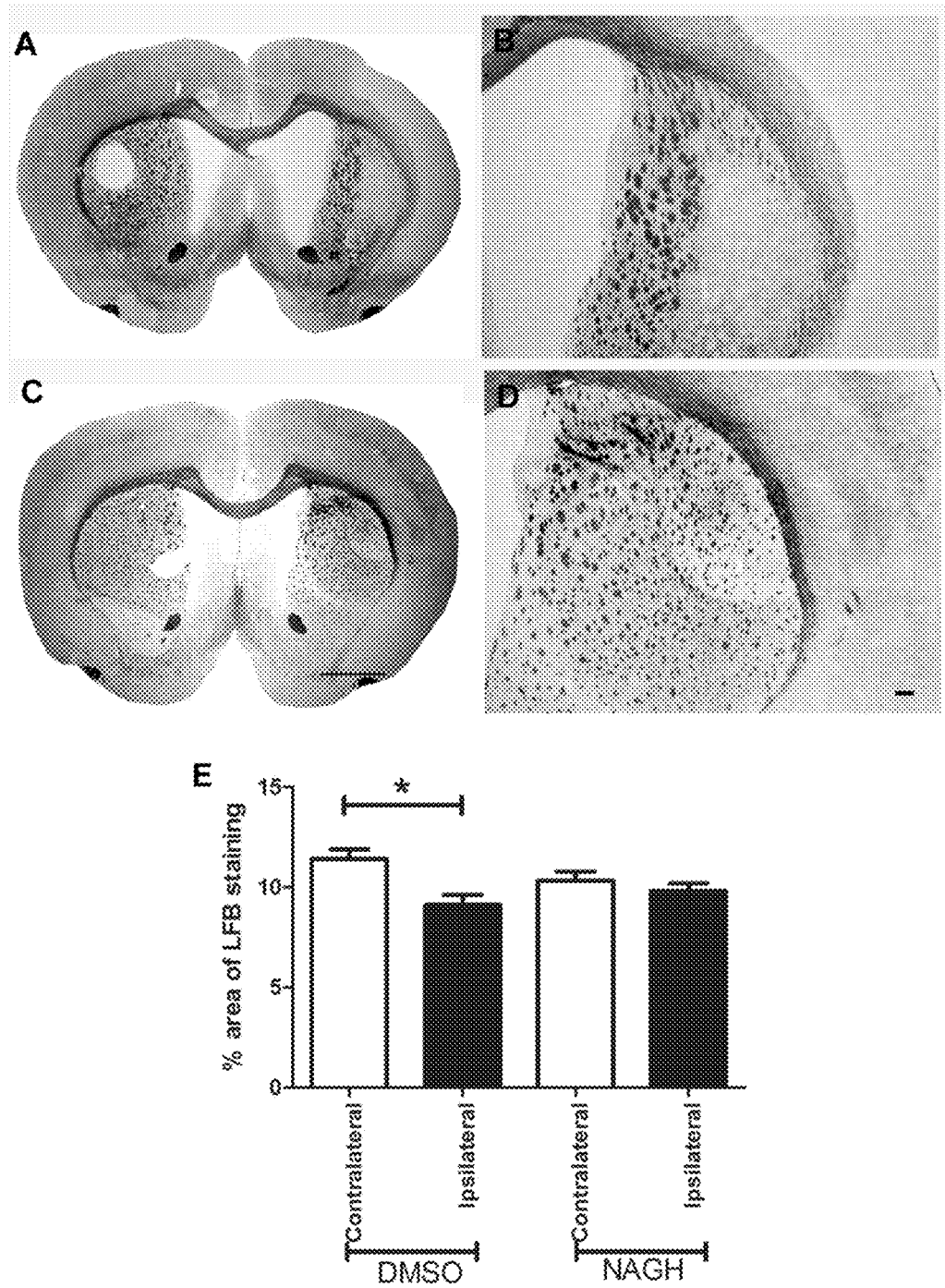
FIG. 6 is a series of images depicting the effects of NAGH on myelinating oligodendrocytes. Luxol Fast blue stained brain from DMSO treated animal revealed reduced staining in the cortex and striatum (A and B) compared with those of NAGH treated animals (C and D). (E), the quantification of the percentage of white matter area stained by LFB of the each hemisphere. Values are mean±SE. *p<0.05 vs. DMSO. Scale bar=100 μm.

With regard to infarct volume, NAGH protected both neurons and oligodendrocytes from MCAO-induced cell death. Infarct size was significantly less in the treated group (*p<0.05). (FIG. 5) Similarly, Luxol Fast blue demonstrated that white matter tracts were more intact in the treated group, particularly in cortex. (FIG. 6)

As such, NAGH is a promising drug that appears to have long-term clinical efficacy as a treatment for stroke. NAGH may protect mature oligodendrocyte damage following MCAO which is a promising therapeutic approach to restore myelin.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods for treatment of stroke, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall there between.

What is claimed is:

1. A method of treating stroke occurring in a brain of a patient in need thereof at a delayed timepoint comprising: administering a therapeutically effective amount of a sigma agonist selected from the group consisting of N,N'-di-1-Naphthylguanidine hydrochloride (NAGH) or N,N'-di-p-Nitrophenylguanidine hydrochloride (NAD) to the patient in need thereof.

2. The method of claim 1, wherein the sigma agonist is administered at least 12 hours after stroke.

3. The method of claim 1, wherein the sigma agonist is NAGH.

4. The method of claim 3, wherein the therapeutically effective amount is between about 0.86 mg/kg and 8.6 mg/kg.

5. The method of claim 4, wherein the NAGH is administered at least once per day.

6. The method of claim 5, wherein the NAGH is administered for at least 3 days.

7. The method of claim 1, wherein the sigma agonist is NAD.

8. The method of claim 7, wherein the therapeutically effective amount is between about 2.8 mg/kg and 8.6 mg/kg.

9. The method of claim 8, wherein the NAD is administered at least once per day.

10. The method of claim 9, wherein the NAD is administered for at least 3 days.

11. A method of reducing infarct volume long term in a patient suffering from a neurological disorder affecting a brain of the patient comprising: administering a therapeutically effective amount of a sigma agonist selected from the group consisting of N,N'-di-1-Naphthylguanidine hydrochloride (NAGH) or N,N'-di-p-Nitrophenylguanidine hydrochloride (NAD) to a patient in need thereof at a delayed timepoint.

12. The method of claim 11, wherein the neurological disorder is stroke.

13. The method of claim 11, wherein the sigma agonist is administered at least 12 hours after stroke.

14. The method of claim 11, wherein the sigma agonist is NAGH.

15. The method of claim 14, wherein the therapeutically effective amount is between about 0.86 mg/kg and 8.6 mg/kg.

16. The method of claim 15, wherein the NAGH is administered at least once per day.

17. The method of claim 16, wherein the NAGH is administered for at least 3 days.

18. The method of claim 11, wherein the sigma agonist is NAD.

19. The method of claim 18, wherein the therapeutically effective amount is between about 2.8 mg/kg and 8.6 mg/kg.

20. The method of claim 19, wherein the NAD is administered at least once per day.

* * * * *